US008349853B2

(12) United States Patent
Bamdad

(10) Patent No.: US 8,349,853 B2
(45) Date of Patent: Jan. 8, 2013

(54) COMPOSITIONS AND METHODS OF TREATMENT OF CANCER

(75) Inventor: Cynthia C. Bamdad, Newton, MA (US)

(73) Assignee: Minerva Biotechnologies Corporation, Waltham, MA (US)

( * ) Notice: Subject to any disclaimer, the term of this patent is extended or adjusted under 35 U.S.C. 154(b) by 184 days.

(21) Appl. No.: 10/237,150

(22) Filed: Sep. 5, 2002

(65) Prior Publication Data

US 2003/0130293 A1 Jul. 10, 2003

Related U.S. Application Data

(60) Provisional application No. 60/317,302, filed on Sep. 5, 2001, provisional application No. 60/376,732, filed on May 1, 2002.

(51) Int. Cl.
*A61K 31/517* (2006.01)
*C07D 239/72* (2006.01)

(52) U.S. Cl. ............... 514/266.31; 544/287; 544/290

(58) Field of Classification Search ............... 514/266.3, 514/266.31; 544/287, 290
See application file for complete search history.

(56) References Cited

U.S. PATENT DOCUMENTS

| 5,561,133 | A | | 10/1996 | Bisset et al. | |
|---|---|---|---|---|---|
| 5,686,621 | A | | 11/1997 | Clark et al. | |
| 5,756,502 | A | * | 5/1998 | Padia | 514/248 |
| 5,866,587 | A | | 2/1999 | de Nanteuil et al. | |
| 6,028,075 | A | | 2/2000 | Pines et al. | |
| 6,319,915 | B1 | | 11/2001 | Goldstein | |
| 6,545,004 | B1 | * | 4/2003 | Finer et al. | 514/266.2 |
| 6,683,108 | B1 | * | 1/2004 | Baxter et al. | 514/443 |
| 6,794,379 | B2 | * | 9/2004 | Medina et al. | 514/183 |
| 2001/0046997 | A1 | | 11/2001 | Abraham et al. | |

FOREIGN PATENT DOCUMENTS

| DE | 23 51 724 A1 | 5/1974 |
|---|---|---|
| EP | 0 447 116 A1 | 9/1991 |
| EP | 0 625 507 A2 | 11/1994 |
| FR | 2 100 726 A | 3/1972 |
| JP | 07 258224 A | 10/1995 |
| WO | WO 00/77031 A2 | 12/2000 |
| WO | WO 01/16114 A2 | 3/2001 |
| WO | WO 01/19800 A2 | 3/2001 |
| WO | WO 01/30768 A1 | 5/2001 |
| WO | WO 02/056022 A2 | 7/2002 |
| WO | WO 02/064590 A | 8/2002 |
| WO | WO 02/064590 A2 | 8/2002 |
| WO | WO 03/020279 A2 | 3/2003 |
| WO | WO 03/020280 A2 | 3/2003 |

OTHER PUBLICATIONS

McMahon et al.*
Pinedo et al.*
McMahon et al., The Oncologist 2000;5(suppl 1):3-10.*
Pinedo et al., The Oncologist 2000;5(suppl 1):1-2.*
Database Chemcats Online!, AN 2000: 855507, "ComGenex Product List", Sep. 16, 1999, XP002227206, abstract.
Database Chemcats Online!, AN 2001: 842059, "ComGenex Product List", Sep. 16, 1999, XP002240398, abstract.
Database Chemcats Online!, AN 2001: 897479, "ComGenex Product List", Sep. 16, 1999, XP002240399, abstract.
Database Chemcats Online!, AN 2001: 843981, "ComGenex Product List", Nov. 16, 1999, XP002240400, abstract.
Database Chemcats Online!, AN 2001: 837276, "ComGenex Product List", Sep. 16, 1999, XP002240401, abstract.
Database Chemcats Online!, AN 2001: 665548, "ComGenex Product List", Sep. 16, 1999, XP002240402, abstract.
Database Chemcats Online!, AN 2001: 665505, "ComGenex Product List", Sep. 16, 1999, XP002240403, abstract.
Database Chemcats Online!, AN 2000: 857046, "ComGenex Product List", Sep. 16, 1999. XP002240404, abstract.
Database ChemcatsOnline!, AN 2001: 829633, "ComGenex Product List", Sep. 16, 1999. XP002225284, abstract.
Database Chemcats Online!, AN 2000: 1038396, "ComGenex Product List", Sep. 16. 1999, XP002225285, abstract.
Database Chemcats Online!, AN 2000: 1038566, "ComGenex Product List", Sep. 16, 1999, XP002225286, abstract.
Database Chemcats Online!, AN 2001: 841794, "ComGenex Product List", Nov. 16, 1999, XP002225287, abstract.
Database Chemcats Online!, AN 2001: 2506326, "ComGenex Product List", Sep. 16, 1999, XP002237602, abstract.
Database Chemcats Online!, AN 2001: 2506309, "ComGenex Product List", Sep. 11, 1999, XP002237603, abstract.
Database Chemcats Online!, AN 2000: 856513, "ComGenex Product List", Sep. 11, 1999, XP002237604, abstract.
Database Chemcats Online!, AN 2001: 849388, "ComGenex Product List". Sep. 16. 1999, XP002237605, abstract.
Amine, M S, "Uses of quinazolin-2-[( -propionoly)isothiocyanate]-4-one as a building block in synthesis of some heterocyclic compounds of expected biological activity", Indian Journal of Chemistry, Nov. 1998, vol. 37B, pp. 1153-1156.
Gagliardi, A., et al., "Inhibition of angiogenesis by suramin", Cancer Research, American Association for Cancer Research, Sep. 15, 1992, No. 18, pp. 5073-5075. Gariepy et al., "Identification of Short Peptide Ligands that Bind Specifically to the Breast Tumor-Associated MUC1 Epitope," Proceedings of the Annual Meeting of the American Association for Cancer Research, American Association for Cancer Research 41:101-102, Mar. 1, 2000.
Database Registry XP-002633668, Chemical Abstracts Service, May 10, 2001.
Database Registry XP-002633669, Chemical Abstracts Service, May 10, 2001.
Database Registry XP-002633670, Chemical Abstracts Service, May 8, 2001.
Database Registry XP-002633771, Chemical Abstracts Service, Apr. 9, 2001.
Database Registry XP-002633772, Chernicai Abstracts Service, May 8, 2001.

* cited by examiner

*Primary Examiner* — Paul V. Ward
(74) *Attorney, Agent, or Firm* — Joseph Hyosuk Kim; JHK Law

(57) ABSTRACT

This invention generally relates to compositions and methods for cancer treatment and, in particular, to compositions able to interact (e.g., bind to) with MUC1 growth factor receptor or its ligands, and methods for treating the same. The invention also relates to assays or use of such compositions for the treatment of patients susceptible to or exhibiting symptoms characteristic of cancer or tumorigenesis. Other compositions of the present invention useful for the treatment or prevention of cancer or tumorigenesis include homologs, analogs, derivatives, enantiomers or functional equivalents. The present compositions can also be packaged in kits in some cases.

41 Claims, 2 Drawing Sheets

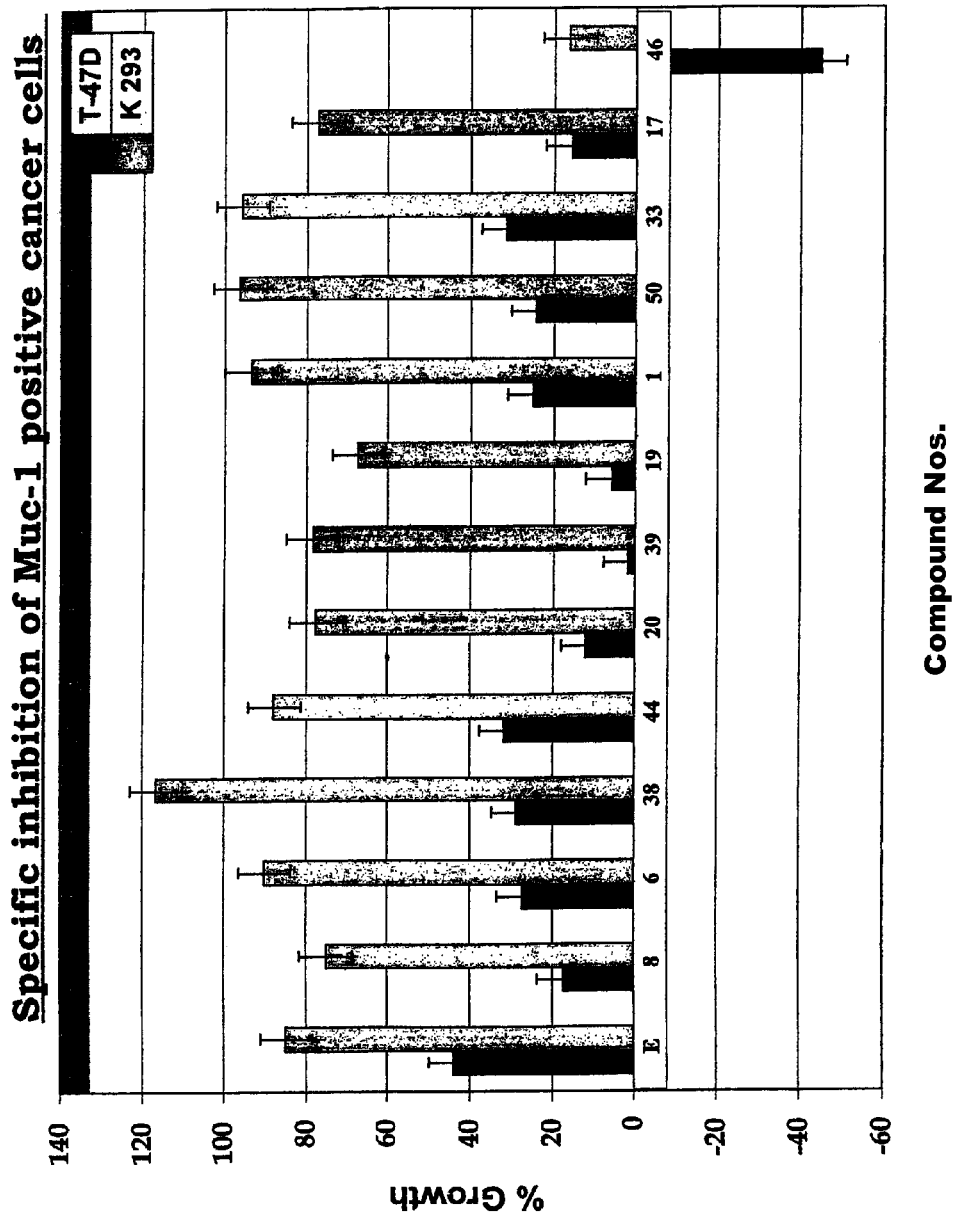

COMPOSITIONS AND METHODS OF TREATMENT OF CANCER

RELATED APPLICATIONS

This non-provisional application claims the benefit under Title 35, U.S.C. §119(e) of U.S. Provisional Patent Application No. 60/317,302, filed Sep. 5, 2001, entitled "Compositions and Methods of Treatment of Cancer," by C. Bamdad, et al.; and U.S. Provisional Patent Application No. 60/376,732, filed May 1, 2002, entitled "Compositions and Methods of Treatment of Cancer," by C. Bamdad, et al. These applications are incorporated herein by reference.

FIELD OF THE INVENTION

This invention generally relates to compositions and methods for cancer treatment and, in particular, to compositions able to interact with MUC1 Growth Factor Receptor or its ligands, and methods for treating the same.

DESCRIPTION OF THE RELATED ART

Many biomolecular interactions that promote tumorigenesis involve cell surface proteins that can mediate intra- or intercellular signaling. The tumor markers generally are proteins on the surface of a cell that may become exclusively expressed, overexpressed, or show an altered expression pattern, as a result of transformation of the cell to a neoplastic state. The surface concentration of certain tumor markers has been correlated with the progression of cancer. For example, the interaction between the integrin cell surface receptor alpha-v-beta-3 ($\alpha_v\beta_3$) and the cell adhesion molecule vitronectin has been implicated in angiogenesis, and the increased concentration of alpha-v-beta-3 on melanoma cells has been correlated with poor prognosis.

Cell surface receptors that have been linked to cancer make up an important class of therapeutic targets. Many pharmaceutical companies are actively involved in screening drug libraries for compounds that bind to and block these cell surface receptors. For example, an important drug used to treat breast cancer is Herceptin. This drug is believed to be able to bind to and block HER2/neu, which is a cell surface receptor overexpressed in about 30% of breast tumors.

Another cell surface receptor, MUC1, is interesting since it is believed to be aberrantly expressed in many human tumors, including about 80% or 90% of breast tumors, and in a significant percentage of other human tumors, such as prostate, lung, ovarian, colorectal, and perhaps brain cancer. On healthy secretory epithelium, MUC1 is believed to be clustered at the apical border of the epithelium and is not significantly expressed in other portions of the cell. However, in tumor cells, the receptor is generally overexpressed homogeneously over the majority of the cell surface, rather than primarily at the apical border. It is also believed that women with breast cancer may have elevated levels of shed MUC1 receptor in their blood. Levels of shed MUC1 receptor in blood serum thus can be measured to track breast cancer in breast cancer patients, for example, to determine recurrence of the disease. However, the method is generally too variable and insensitive to be used as a diagnostic tool.

Until now, the mechanistic link between the MUC1 receptor and tumorigenesis has not been well understood. Attempts to correlate the number of repeat units (which can vary from person to person) with the susceptibility to cancer have generally failed. Investigations of a possible connection between glycosylation of the MUC1 receptor and cancer have produced conflicting and inconsistent results. Importantly, until now, functional ligands for the extracellular portion of the MUC1 receptor have not been identified.

Absent an understanding of the biological mechanism of action of the MUC1 receptor, and how the MUC1 receptor is able to trigger tumorigenesis, it has not been possible to design or identify therapeutics that interfere with the disease-associated function of this receptor. Indeed, there is no drug currently in use or, to our knowledge, in clinical trials, that is known to target the MUC1 receptor.

SUMMARY OF THE INVENTION

This invention generally relates to compositions that are able to inhibit interactions involving the MUC1 Growth Factor Receptor or its ligands, and methods for treating patients displaying symptoms of, or susceptible to MUC1-associated cancers. The subject matter of this application involves, in some cases, interrelated products, alternative solutions to a particular problem, and/or a plurality of different uses of a single system or article.

Several methods are disclosed herein of administering to a subject a composition for prevention or treatment of a particular condition. It is to be understood that in each such aspect of the invention, the invention specifically includes the composition for use in the treatment or prevention of that particular condition, as well as use of the composition for the manufacture of a medicament for the treatment or prevention of that particular condition. In some aspects of the invention, the invention also includes a pharmaceutically acceptable carrier.

The present invention includes methods of treatment of selected groups of patients. It is to be understood that all compositions described herein are useful for each described method.

Also included in the present invention is a combinatorial approach in which structural features identified as characteristic of compositions effective for treatment at various disease stages are used as the basis for combinatorial synthesis of a wide variety of structural homologs, analogs, derivatives, enantiomers and functionally equivalent compositions thereof, for identification of a wide variety of compositions useful for treatment MUC1-associated cancers. Thus, in one embodiment, the invention involves providing any one of compositions 1-51, performing a combinatorial synthesis resulting in a plurality of compositions. Then, one can perform an assay involving the plurality of the compositions to determine their effectiveness in cancer treatment, specifically, treatment of cancers disclosed herein. Compositions 1-51 also can be altered using medicinal chemistry techniques.

Another aspect of the invention provides a pharmaceutical preparation comprising a composition comprising any of the compositions 1-51, and a pharmaceutically active carrier. In one embodiment, the composition comprises homologs, analogs, derivatives, enantiomers and functionally equivalent compositions thereof of compositions 1-51. In all structures herein, atom locations, if unlabeled, are carbon with appropriate hydrogen(s).

The invention also provides a method involving promoting the prevention or treatment of MUC1-associated cancer via administration of any one of the compositions of the present invention and homologs, analogs, derivatives, enantiomers and functionally equivalent compositions thereof.

In another aspect the invention provides a kit including any one of the compositions of the present invention and homologs, analogs, derivatives, enantiomers and functionally equivalent compositions thereof; and instructions for use of these compositions for treatment of cancer characterized by aberrant expression of MUC1.

In one aspect, the invention includes a composition. In one set of embodiments, the composition has a structure:

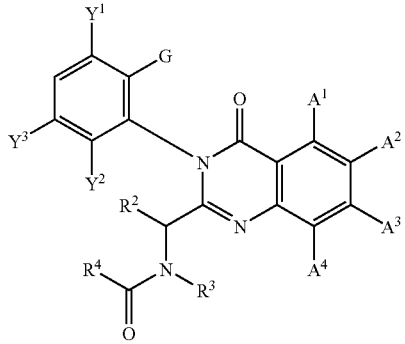

where $A^1$, $A^2$, $A^3$, $A^4$, $Y^1$, $Y^2$, and $Y^3$ can each be independently selected from the group consisting of H and a halogen, G can be a group having one carbon only, optionally in combination with other atoms (e.g. methoxy), and $R^2$, $R^3$ and $R^4$ each independently comprise at least one atom. In one embodiment, each of $A^1$, $A^2$, $A^3$, $A^4$, $Y^1$, $Y^2$, and $Y^3$ can be H, G can be methyl or methoxy, $R^2$ can be methyl or ethyl, $R^3$ can be a cyclic aromatic or an alkyl of from 2-6 carbon atoms, and $R^4$ can be —NHR5, where R5 can be a cyclic aromatic, optionally substituted.

In another set of embodiments, the composition has a structure:

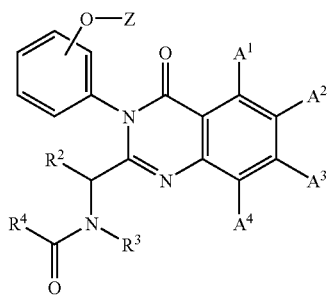

where $A^1$, $A^2$, $A^3$ and $A^4$ can each be independently selected from the group consisting of H, methyl, or a halogen, Z comprises at least three carbon atoms, and $R^2$, $R^3$ and $R^4$ each independently comprise at least one atom. —O—Z, as depicted, can be bound to any of the available verticies of the ring from which it emanates. This interpretation applies to other, similarly-depicted structures herein. In one embodiment, each of $A^1$, $A^2$, $A^3$, $A^4$ can be H, methyl, or a halogen, $R^1$ comprises a cyclic aromatic, $R^2$ can be methyl or ethyl, $R^3$ and $R^4$ each includes a cyclic aromatic.

In another set of embodiments, the composition has a structure:

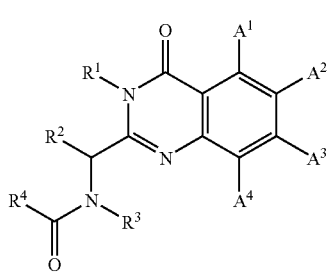

where $A^1$, $A^2$, $A^3$ and $A^4$ can each be independently selected from the group consisting of H, methyl, or a halogen, $R^1$, $R^2$, and $R^4$ each independently comprise at least one atom, and $R^3$ comprises a branched alkyl group or at least 6 carbon atoms. In one embodiment, $A^1$, $A^2$, $A^3$, $A^4$ can each be H, $R^1$ can be an aromatic group, $R^2$ can be methyl or ethyl, $R^3$ includes a cyclic aromatic, and $R^4$ includes a cyclic aromatic or two fused rings or can be an alkyl group of from 1-4 carbon atoms substituted with 2 halogens.

In another set of embodiments, the composition has a structure:

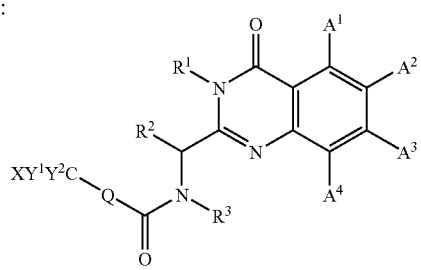

where $A^1$, $A^2$, $A^3$, and $A^4$, $Y^1$, and $Y^2$ can each be independently selected from the group consisting of H, methyl, or a halogen, $R^1$, $R^2$ and $R^3$ each independently comprise at least one atom, Q comprises a chemical bond or an alkyl group, and X comprises a halogen. In one embodiment, $A^1$, $A^2$, $A^3$, and $A^4$ can each be H, $R^1$ can be an aromatic group, $R^2$ can be methyl or ethyl, $R^3$ can be an alkyl group, branched in one embodiment, Q can be a chemical bond, X can be chlorine, $Y^1$ can be chlorine, and $Y^2$ can be hydrogen.

In another set of embodiments, the composition has a structure:

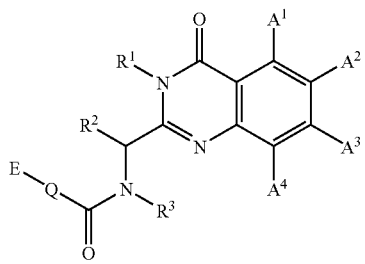

where $A^1$, $A^2$, $A^3$ and $A^4$ can each be independently selected from the group consisting of H, methyl, or a halogen, $R^1$, $R^2$, and $R^3$ each independently comprise at least one atom, Q comprises a chemical bond or an alkyl group, and E comprises at least 2 cyclic groups in a branched configuration. In one embodiment, each of $A^1$, $A^2$, $A^3$, $A^4$ can be H, methyl, or a halogen, $R^1$ can be an aromatic group, $R^2$ can be methyl or ethyl, $R^3$ can be an alkyl group or cyclic structure, Q can be a chemical bond, E includes at least two aromatic groups, and in one embodiment can be diphenyl methyl.

In another set of embodiments, the composition has a structure:

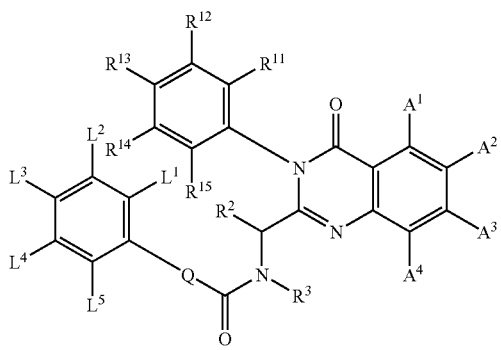

where $A^1$, $A^2$, $A^3$ and $A^4$ can each be independently selected from the group consisting of H, methyl, or a halogen, $R^2$, $R^3$, $R^{11}$, $R^{12}$, $R^{13}$, $R^{14}$, and $R^{15}$ each independently comprise at least one atom, Q comprises a chemical bond or an alkyl group, and at least two of $L^1$, $L^2$, $L^3$, $L^4$, and $L^5$ can be interconnected via a saturated moiety. In one embodiment, each of $A^1$, $A^2$, $A^3$, $A^4$ can be H, methyl, or a halogen, $R^2$ can be methyl or ethyl, each of $R^{11}$, $R^{12}$, $R^{14}$, $R^{15}$ can be H, $R^{13}$, a halogen (in one embodiment bromine) or alkyl of from 1-4 carbons (in one embodiment methyl), $R^3$ can be alkyl of from 1-5 carbons, Q can be a chemical bond, at least two of $L^2$ and $L^3$ can be connected (in one embodiment via a moiety including oxygen), and each of $L^1$, $L^4$, and $L^5$ can be H or methyl.

In another set of embodiments, the composition has a structure:

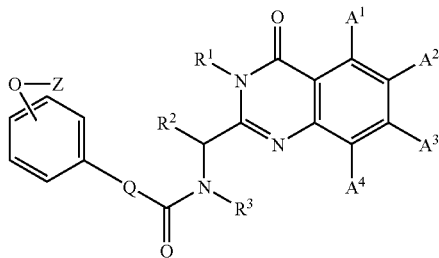

where $A^1$, $A^2$, $A^3$ and $A^4$ can each be independently selected from the group consisting of H, methyl, or a halogen, $R^1$, $R^2$, and $R^3$ each independently comprise at least one atom, Q comprises a chemical bond or an alkyl group, and Z comprises at least one carbon atom. In one embodiment, each of $A^1$, $A^2$, $A^3$, $A^4$ can be H, methyl, or a halogen, $R^2$ can be methyl or ethyl, $R^3$ can be alkyl of from 1-8 carbons, Q can be a chemical bond, and Z can be methyl or ethyl.

In another set of embodiments, the composition has a structure:

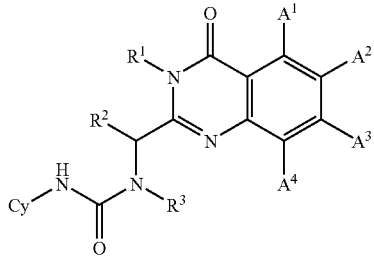

where $A^1$, $A^2$, $A^3$ and $A^4$ can each be independently selected from the group consisting of H, methyl, and a halogen, $R^1$, $R^2$, and $R^3$ each independently comprise at least one atom, and Cy comprises a non-aromatic structure. In one embodiment, each of $A^1$, $A^2$, $A^3$, $A^4$ can be H, methyl, or a halogen, $R^2$ can be methyl or ethyl, $R^1$ can be H or methyl, and Cy can be cyclohexyl.

In another set of embodiments, the composition has a structure:

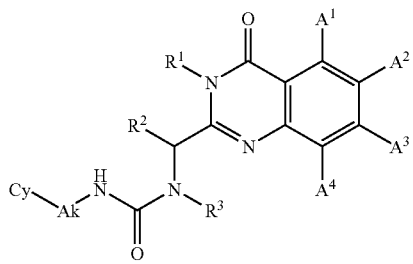

where $A^1$, $A^2$, $A^3$ and $A^4$ can each be independently selected from the group consisting of H and a halogen, $R^1$, $R^2$, and $R^3$ each independently comprise at least one atom, Ak comprises an alkyl group, and Cy comprises a cyclic structure. In one embodiment, each of $A^1$, $A^2$, $A^3$, $A^4$ can be H, methyl, or a halogen, $R^2$ can be methyl or ethyl, $R^1$ can be aromatic, $R^3$ includes from 3-9 carbons, Cy can be an aromatic, and Ak includes from 2-4 carbons.

In another set of embodiments, the composition has a structure:

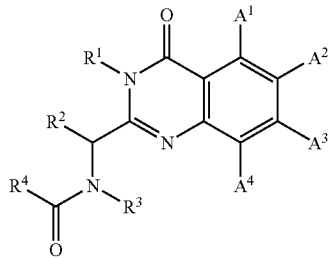

where $A^1$, $A^2$, $A^3$ and $A^4$ can each be independently selected from the group consisting of H and a halogen, $R^1$, $R^2$, and $R^3$ each independently comprise at least one atom, and $R^4$ comprises a multifused cyclic structure. In one embodiment, each of $A^1$, $A^2$, $A^3$, $A^4$ can be H, methyl, or a halogen, $R^2$ can be methyl or ethyl, $R^1$ can be aromatic, $R^3$ can be alkyl (branched in one embodiment), $R^4$ can be adamantane.

In another set of embodiments, the composition has a structure:

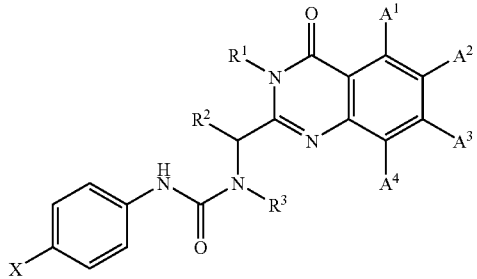

where $A^1$, $A^2$, $A^3$ and $A^4$ can each be independently selected from the group consisting of H and a halogen, $R^1$, $R^2$, and $R^3$ each independently comprise at least one atom, and X comprises a halogen. In one embodiment, each of $A^1$, $A^2$, $A^3$, $A^4$ can be H, methyl, or a halogen, $R^2$ can be methyl or ethyl, $R^1$ can be aromatic, $R^3$ can be alkyl (branched in one embodiment), X can be bromine or chlorine.

In another set of embodiments, the composition has a structure:

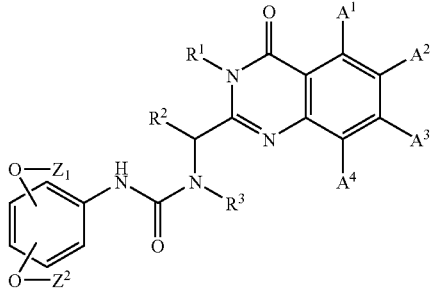

where $A^1$, $A^2$, $A^3$ and $A^4$ can each be independently selected from the group consisting of H and a halogen, $R^1$, $R^2$, and $R^3$ each independently comprise at least one atom, and $Z^1$ and $Z^2$ each independently comprise at least one carbon atom. In one embodiment, each of $A^1$, $A^2$, $A^3$, $A^4$ can be H, methyl, or a halogen, $R^2$ can be methyl or ethyl, $R^1$ can be aromatic (optionally a dihalo aromatic), $R^3$ includes from 5-7 carbons (non-branched alkyl in one embodiment), $Z^1$ and $Z^2$ can be methyl or ethyl.

In another set of embodiments, the composition has a structure:

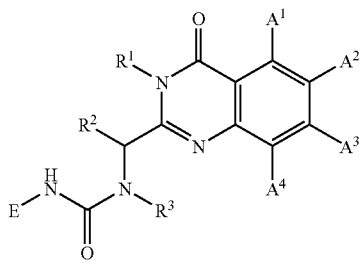

where $A^1$, $A^2$, $A^3$ and $A^4$ can each be independently selected from the group consisting of H and a halogen, $R^1$, $R^2$, and $R^3$ each independently comprise at least one atom, and comprises at least two fused cyclic structures. In one embodiment, each of $A^1$, $A^2$, $A^3$, $A^4$ can be H, methyl, or a halogen, $R^2$ can be methyl or ethyl, $R^1$ can be aromatic, $R^3$ can be alkyl (branched in one embodiment), E can be naphthalenyl.

In another set of embodiments, the composition has a structure:

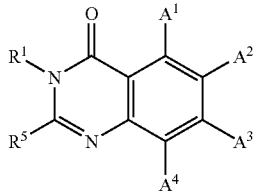

where $A^1$, $A^2$, $A^3$ and $A^4$ can each be independently selected from the group consisting of H and a halogen, $R^1$ comprises at least one atom, and $R^5$ comprises a structure including a unit:

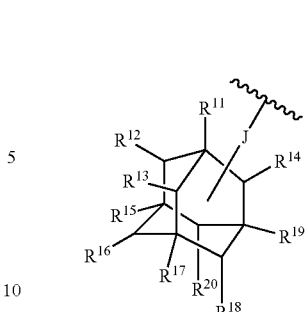

where $R^{11}$, $R^{12}$, $R^{13}$, $R^{14}$, $R^{15}$, $R^{16}$, $R^{17}$, $R^{18}$, $R^{19}$, and $R^{20}$ each independently comprise at least one atom, J comprises a chemical bond or at least one atom, and at least one of $R^{11}$, $R^{12}$, $R^{13}$, $R^{14}$, $R^{15}$, $R^{16}$, $R^{17}$, $R^{18}$, $R^{19}$, and $R^{20}$ can be substituted by J. In one embodiment, J can be a chemical bond, each of $A^1$, $A^2$, $A^3$, $A^4$ can be H, methyl, or a halogen, $R^1$ can be aromatic, each of $R^{11}$-$R^{20}$, other than J, can be H or methyl or halogen (in one embodiment, each can be H). In one embodiment, J comprises at least 5 atoms.

In another set of embodiments, the composition has a structure:

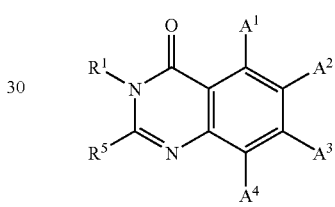

where $A^1$, $A^2$, $A^3$ and $A^4$ can each be independently selected from the group consisting of H and a halogen, $R^1$ comprises at least one atom, and $R^5$ comprises a structure including a unit:

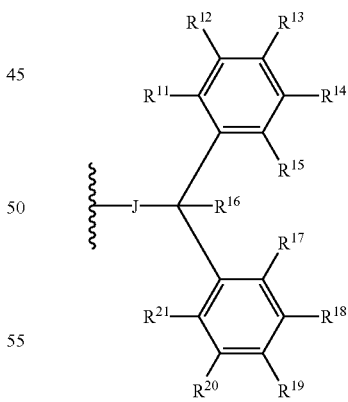

where $R^{11}$, $R^{12}$, $R^{13}$, $R^{14}$, $R^{15}$, $R^{16}$, $R^{17}$, $R^{18}$, $R^{19}$, $R^{20}$ and $R^{21}$ each independently comprise at least one atom, and J comprises a chemical bond or at least one atom. In one embodiment, J can be a chemical bond, each of $A^1$, $A^2$, $A^3$, $A^4$ can be H, methyl, or a halogen or methyl, $R^1$ can be aromatic, each of $R^{11}$-$R^{21}$ can be H or methyl or halogen (in one embodiment, each can be H). In one embodiment, J comprises at least 5 atoms.

In another set of embodiments, the composition has a structure:

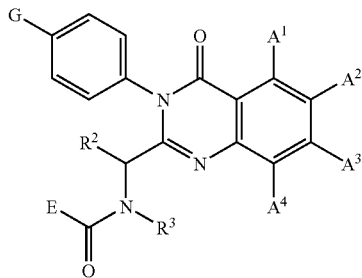

where $A^1$, $A^2$, $A^3$, and $A^4$ can each be independently selected from the group consisting of H and a halogen, G can be selected from the group consisting of —$CH_3$ and a halogen, $R^2$ and $R^3$ each independently comprise at least one atom, and E comprises at least two fused cyclic structures. In one embodiment, each of $A^1$, $A^2$, $A^3$, $A^4$ can be H, methyl, or a halogen, $R^3$ can be alkyl or aromatic, E includes two fused cyclic groups (in one embodiment, one of the cyclic structures can be aromatic).

In another set of embodiments, the composition has a structure:

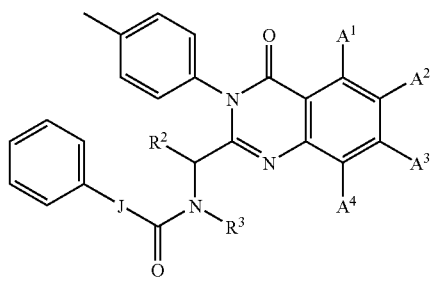

where $A^1$, $A^2$, $A^3$, and $A^4$ can each be independently selected from the group consisting of H and a halogen, $R^2$ and $R^3$ each independently comprise at least one atom, and J comprises a chemical bond or at least one atom. In one embodiment, each of $A^1$, $A^2$, $A^3$, and $A^4$ can be H, methyl, or a halogen, $R^3$ can be alkyl of from 1-7 carbons, or can be aromatic. J includes from 1-8 carbons.

In another set of embodiments, the composition has a structure:

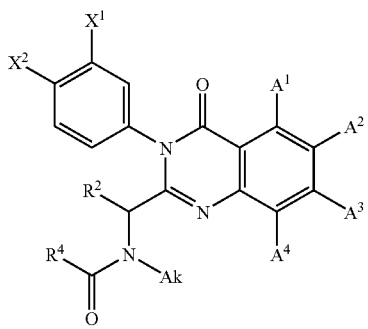

where $A^1$, $A^2$, $A^3$, and $A^4$ can each be independently selected from the group consisting of H and a halogen, $X^1$ and $X^2$ each independently comprise a halogen, Ak can be a non-heteroatom alkyl group or is free of non-terminal heteroatoms, and $R^2$ and $R^4$ each independently comprise at least one atom. In one embodiment, each of $A^1$, $A^2$, $A^3$, $A^4$ can be H, methyl, or a halogen, Ak can be an alkyl of from 5-7 carbons, $R^4$ can be aromatic, $X^1$ and $X^2$ each can be halogens, but can be different.

In another set of embodiments, the composition has a structure:

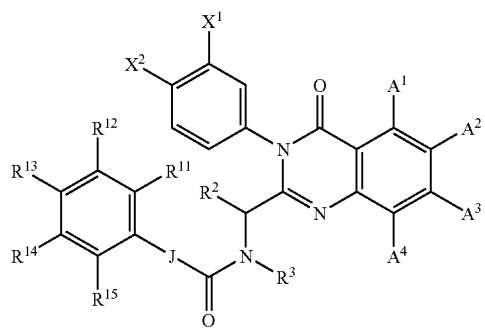

where $A^1$, $A^2$, $A^3$, and $A^4$ can each be independently selected from the group consisting of H and a halogen, $X^1$ and $X^2$ each independently comprise a halogen, J comprises a chemical bond or at least one atom, and $R^2$, $R^3$, $R^{11}$, $R^{12}$, $R^{13}$, $R^{14}$, and $R^{15}$ each independently comprise at least one atom. In one embodiment, each of $A^1$, $A^2$, $A^3$, $A^4$ can be H, methyl, or a halogen, $R^3$ can be an alkyl of from 5-7 carbons, J can be a chemical bond, at least three of $R^{11}$-$R^{15}$ can be H (in one embodiment each of $R^{11}$ and $R^{13}$ can be an oxygen-containing alkyl of no more than 3 carbon atoms, and in another embodiment $R^{13}$ can be alkyl of no more than 3 carbons and $R^{11}$ can be H).

In another set of embodiments, the composition has a structure:

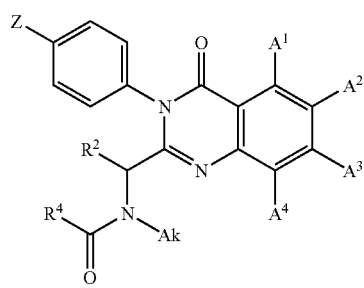

where $A^1$, $A^2$, $A^3$, and $A^4$ can each be independently selected from the group consisting of H and a halogen, Z can be selected from the group consisting of H and —$CH_2$—$CH_3$, Ak can be a non-heteroatom alkyl group or is free of non-terminal heteroatoms, and $R^2$ and $R^4$ each independently comprise at least one atom. In one embodiment, each of $A^1$, $A^2$, $A^3$, $A^4$ can be H, methyl, or a halogen, $R^2$ can be methyl or ethyl, Ak can be alkyl of from 3-7 carbons (non-branched in one embodiment), $R^4$ can be aromatic, Z can be H or ethyl.

In another set of embodiments, the composition has a structure:

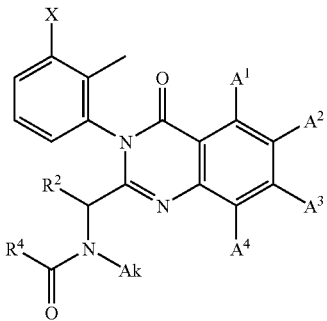

where $A^1$, $A^2$, $A^3$, and $A^4$ can each be independently selected from the group consisting of H and a halogen, X comprises a halogen, Ak can be a non-heteroatom alkyl group or is free of non-terminal heteroatoms, and $R^2$ and $R^4$ each independently comprise at least one atom. In one embodiment, each of $A^1$, $A^2$, $A^3$, $A^4$ can be H, methyl, or a halogen, $R^2$ can be methyl or ethyl, Ak can be alkyl of from 3-7 carbons (non-branched in one embodiment), $R^4$ can be aromatic, X can be chlorine.

In another set of embodiments, the composition has a structure:

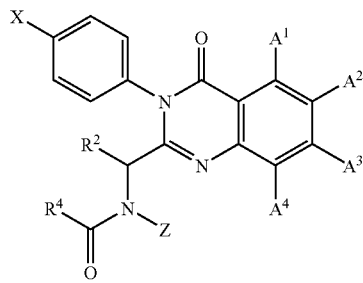

where $A^1$, $A^2$, $A^3$ and $A^4$ can each be independently selected from the group consisting of H and a halogen, X comprises a halogen, Z comprises an alkyl group having at least three carbon atoms, and $R^2$, $R^3$ and $R^4$ each independently comprise at least one atom. In one embodiment, each of $A^1$, $A^2$, $A^3$, $A^4$ can be H, methyl, or a halogen, $R^2$ can be methyl or ethyl, Z can be alkyl of from 3-7 carbons (non-branched in one embodiment), $R^4$ can be aromatic, X can be chlorine or bromine.

In another set of embodiments, the composition has a structure:

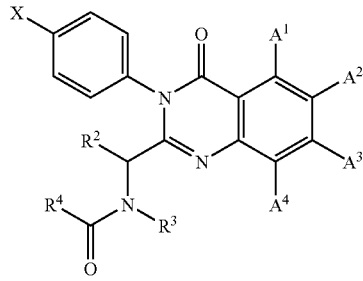

where $A^1$, $A^2$, $A^3$, and $A^4$ can each be independently selected from the group consisting of H and a halogen, X comprises a halogen, $R^3$ comprises a structure including at least two halogen atoms, and $R^2$ and $R^4$ each independently comprise at least one atom. In one embodiment, each of $A^1$, $A^2$, $A^3$, $A^4$ can be H, methyl, or a halogen, $R^2$ can be methyl or ethyl, $R^3$ can be alkyl including at least 2 halogens (optionally aromatic including at least two halogens), $R^4$ can be aromatic, X can be chlorine or bromine.

In another set of embodiments, the composition has a structure:

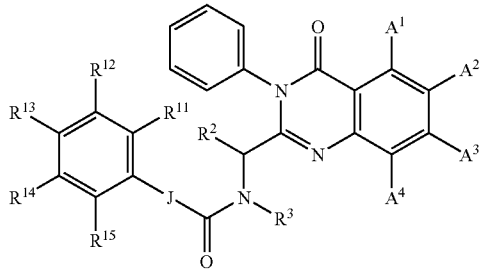

where $A^1$, $A^2$, $A^3$, and $A^4$ can each be independently selected from the group consisting of H and a halogen, J comprises a chemical bond or at least one atom, and $R^2$, $R^3$, $R^{11}$, $R^{12}$, $R^{13}$, $R^{14}$, and $R^{15}$ each independently comprise at least one atom. In one embodiment, each of $A^1$, $A^2$, $A^3$, $A^4$ can be H, methyl, or a halogen, $R^2$ can be methyl or ethyl, $R^3$ can be alkyl of from 2-7 carbons, J can be a chemical bond, $R^{13}$ can be methoxy, other R groups can be H, methyl, or halogen.

In another set of embodiments, the composition has a structure:

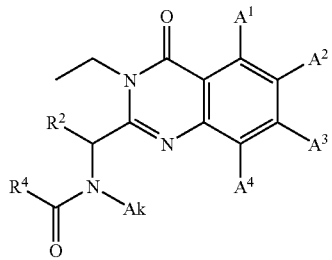

where $A^1$, $A^2$, $A^3$, and $A^4$ can each be independently selected from the group consisting of H and a halogen, Ak can be a non-heteroatom alkyl group or is free of non-terminal heteroatoms, and $R^2$ and $R^4$ each independently comprise at least one atom. In one embodiment, each of $A^1$, $A^2$, $A^3$, $A^4$ can be H, methyl, or a halogen, Ak can be alkyl of from 3-5 carbons, $R^4$ can be aromatic. $R^2$ can be methyl or ethyl.

In another set of embodiments, the composition has a structure:

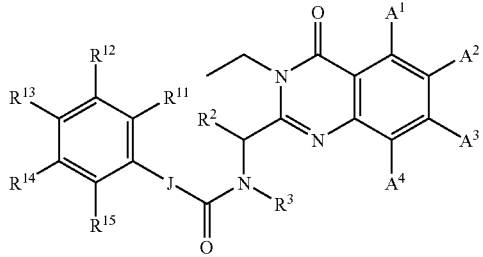

where $A^1$, $A^2$, $A^3$, and $A^4$ can each be independently selected from the group consisting of H and a halogen, J comprises a chemical bond or at least one atom, and $R^2$, $R^3$, $R^{11}$, $R^{12}$, $R^{13}$, $R^{14}$, and $R^{15}$ each independently comprise at least one atom. In one embodiment, each of $A^1$, $A^2$, $A^3$, $A^4$ can be H, methyl, or a halogen, $R^3$ can be alkyl of from 3-5 carbons, J can be a chemical bond, $R^2$ can be methyl or ethyl, $R^{13}$ can be methoxy, and other R groups can be H, halogen, or methyl.

In another set of embodiments, the composition has a structure:

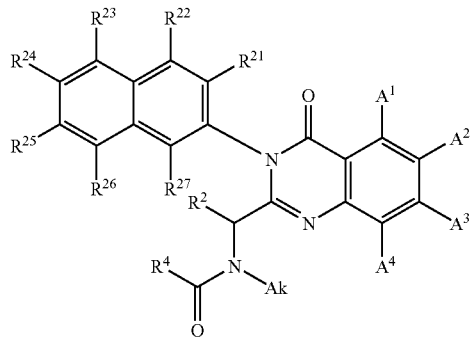

where $A^1$, $A^2$, $A^3$, and $A^4$ can each be independently selected from the group consisting of H and a halogen, Ak can be a non-heteroatom alkyl group or is free of non-terminal heteroatoms, and $R^2$, $R^4$, $R^{21}$, $R^{22}$, $R^{23}$, $R^{24}$, $R^{25}$, $R^{26}$, and $R^{27}$ each independently comprise at least one atom. In one embodiment each of $A^1$-$A^4$ and $R^{21}$-$R^{27}$ can be H, methyl, or a halogen, Ak can be alkyl of from 3-5 carbons, $R^4$ can be aromatic, and $R^2$ can be methyl or ethyl.

In another set of embodiments, the composition has a structure:

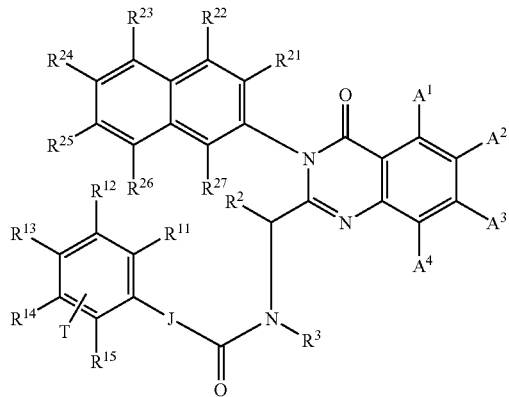

where $A^1$, $A^2$, $A^3$, and $A^4$ can each be independently selected from the group consisting of H and a halogen, J comprises a chemical bond or at least one atom, $R^2$, $R^3$, $R^{11}$, $R^{12}$, $R^{13}$, $R^{14}$, $R^{15}$, $R^{21}$, $R^{22}$, $R^{23}$, $R^{24}$, $R^{25}$, $R^{26}$, and $R^{27}$ each independently comprise at least one atom, and at least one of $R^{11}$, $R^{12}$, $R^{13}$, $R^{14}$, and $R^{15}$ can be substituted by T, T comprising at least one carbon atom. In one embodiment, J can be a chemical bond, each of $A^1$-$A^4$ and $R^{21}$-$R^{27}$ can be H, methyl, or a halogen, $R^3$ can be methyl or ethyl, J can be a chemical bond, each of $R^{11}$-$R^{15}$ that is not substituted by T can be H, methyl, or a halogen (in one embodiment, H), and T can be methoxy, ethoxy, or isopropxy (in one embodiment, methoxy).

In another set of embodiments, the composition has a structure:

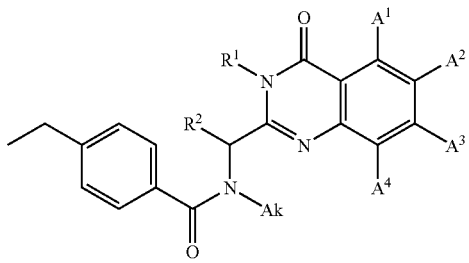

where $A^1$, $A^2$, $A^3$, and $A^4$ can each be independently selected from the group consisting of H and a halogen, $R^1$ and $R^2$ each independently comprise at least one atom, and Ak can be a non-heteroatom alkyl group or is free of non-terminal heteroatoms. In one embodiment, each of $A^1$-$A^4$ can be H, methyl, or a halogen, $R^1$ can be aromatic (in one embodiment, halogen-substituted), $R^2$ can be methyl or ethyl, Ak can be alkyl of from 4-9 carbons.

In another set of embodiments, the composition has a structure:

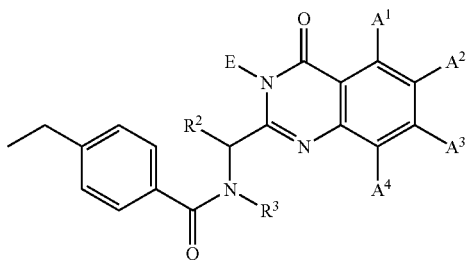

where $A^1$, $A^2$, $A^3$, and $A^4$ can each be independently selected from the group consisting of H and a halogen, E comprises at least 2 cyclic groups, and $R^2$ and $R^3$ each independently comprise at least one atom.

In another set of embodiments, the composition has a structure:

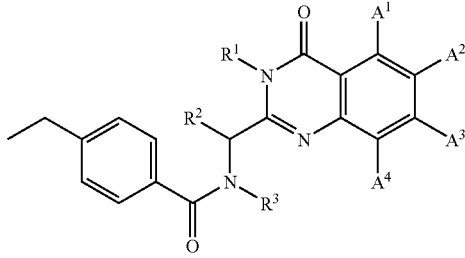

where $A^1$, $A^2$, $A^3$, and $A^4$ can each be independently selected from the group consisting of H and a halogen, $R^1$ comprises a structure including at least two halogen atoms, and $R^2$ and $R^3$ each independently comprise at least one atom.

In another set of embodiments, the composition has a structure:

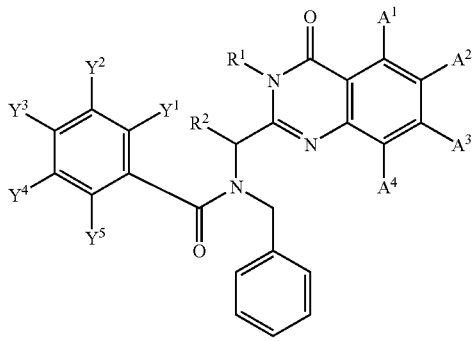

where $A^1$, $A^2$, $A^3$, $A^4$, $Y^1$, $Y^2$, $Y^3$, $Y^4$ and $Y^5$ can each be independently selected from the group consisting of H and a halogen, and $R^1$ and $R^2$ each independently comprise at least one atom. In one embodiment, each of $A^1$-$A^4$ can be H, methyl, or a halogen, $R^1$ can be aromatic (in one embodiment, methoxy-substituted), $R^2$ can be methyl or ethyl, $Y^1$-$Y^4$ can each be H or methyl, with the exception that one can be a halogen.

In another set of embodiments, the composition has a structure:

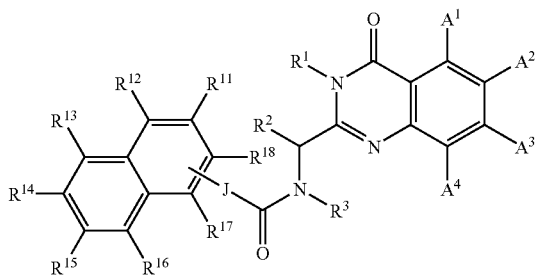

where $A^1$, $A^2$, $A^3$, and $A^4$ can each be independently selected from the group consisting of H and a halogen, J comprises a chemical bond or at least one atom, $R^1$, $R^2$, $R^3$, $R^{11}$, $R^{12}$, $R^{13}$, $R^{14}$, $R^{15}$, $R^{16}$, $R^{17}$, and $R^{18}$ each independently comprise at least one atom, and at least one of $R^{11}$, $R^{12}$, $R^{13}$, $R^{14}$, $R^{15}$, $R^{16}$, $R^{17}$, and $R^{18}$ can be interconnected with J. In one embodiment, each of $A^1$-$A^4$ can be H, methyl, or a halogen, $R^1$ can be aromatic (in one embodiment, halogen-substituted in at least one location), $R^2$ can be methyl or ethyl, $R^3$ can be alkyl of from 2-5 carbons, $R^{11}$-$R^{18}$ can be H or methyl, with the exception of the one at which J bonds. J can be a chemical bond or N.

In another set of composition, the composition has a structure Ak-Aa-Cy, where Ak can be an alkyl group, Aa comprises an amino acid, and Cy comprises a cyclic structure; in combination with a pharmaceutically acceptable carrier. In one set of embodiments, Aa is selected from among glycine, isoleucine, proline, phenylalanine.

In yet another set of embodiments, the composition has a structure $Cy^1$-Aa-$Cy^2$, where Aa comprises an amino acid and $Cy^1$ and $Cy^2$ each independently comprise a cyclic structure. In one set of embodiments, Aa is selected from among proline and phenylalanine.

In another set of embodiments, the composition has a structure:

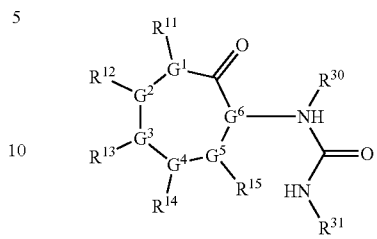

where $R^{11}$, $R^{12}$, $R^{13}$, $R^{14}$, $R^{15}$, $R^{30}$ and $R^{31}$ each independently comprise at least one atom, and $G^1$, $G^2$, $G^3$, $G^4$, $G^5$, and $G^6$ each independently comprise at least one atom able to form at least three covalent bonds; in combination with a pharmaceutically acceptable carrier. In one set of embodiments, each of $R^{11}$, —$R^{15}$ can be H, each of $R^{30}$ and $R^{31}$ includes an aromatic, $G^1$ can be N, and each of $G^2$-$G^6$ can be C and $G^6$ In another set of embodiments, the composition has a structure:

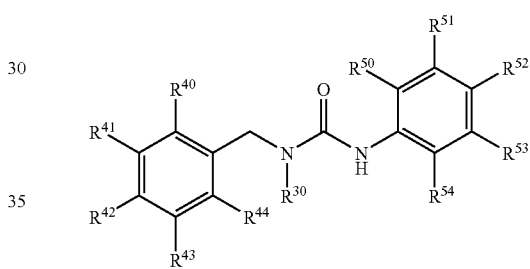

where each of the R groups independently comprises an atom, in combination with a pharmaceutically-acceptable carrier. In one set of embodiments, each of $R^{50}$-$R^{54}$ can be H, each of $R^{40, 41, 43, 44}$ can be H, $R^{42}$ can be t-butyl or ethoxy, $R^{30}$ can be a cyclic structure (in one embodiment, a 7-membered ring).

In another set of embodiments, the composition has a structure:

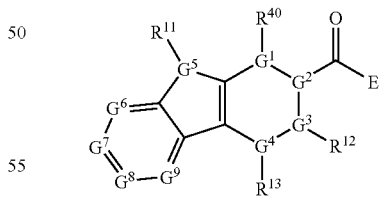

where $R^{11}$, $R^{12}$, $R^{13}$, and $R^{40}$ each independently comprise at least one atom, $G^1$, $G^2$, $G^3$, $G^4$, $G^5$, $G^6$, $G^7$, $G^8$, and $G^9$ each independently comprise at least one atom able to form at least three covalent bonds, and E comprises at least 2 cyclic groups; in combination with a pharmaceutically acceptable carrier. In one set of embodiments, $G^5$ and $G^2$, can be N, and all remaining G groups can be C, each of $R^{11}$, $R^{12}$, $R^{13}$ can be H or methyl, $R^{40}$ can be aromatic (in one embodiment a benzeme or substituted benzene), E comprises naphthalene.

In another set of embodiments, the composition has a structure:

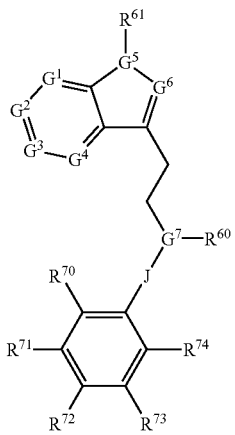

where $R^{60}$, $R^{61}$, $R^{70}$, $R^{71}$, $R^{72}$, $R^{73}$, and $R^{74}$ each independently comprises at least one atom, $G^1$, $G^2$, $G^3$, $G^4$, $G^5$, $G^6$, and $G^7$ each independently comprise at least one atom able to form at least three covalent bonds, and J comprises a chemical bond or at least one atom; in combination with a pharmaceutically acceptable carrier. In one set of embodiments, $G^5$ can be N, each of $G^1$-$G^6$ can be C, $G^7$ can be N, $R^{61}$ can be H, J comprises at least one C, each of $R^{70}$-$R^{74}$ can be H or methyl except that $R^{72}$ can be alkoxy. $R^{60}$ includes at least one halogen, and can be a halogenated alkyl of no more than 3 carbons, or an aromatic (in one embodiment, including at least two fused rings).

In one aspect, the invention is defined, at least in part, by a method. In some embodiments of the invention, the method involves treating a human patient susceptible to or exhibiting symptoms of a cancer characterized by aberrant expression of MUC1 with any of the compositions disclosed herein. In one set of embodiments, the patient is susceptible of, but does not exhibit symptoms of, cancer characterized by aberrant expression of MUC1. In another set of embodiments, the patient exhibits symptoms of cancer characterized by aberrant expression of MUC1. In some embodiments of the method, the patient is not otherwise indicated for treatment for a cancer characterized by aberrant expression of hedgehog.

In one set of embodiments, the method includes the step of administering to a patient a therapeutically effective amount of a composition comprising a structure:

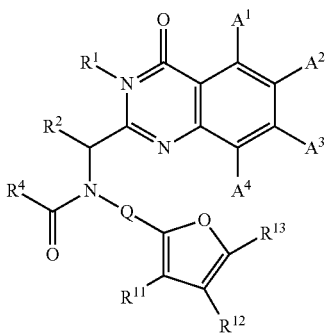

where Q comprises a chemical bond or an alkyl group, $A^1$, $A^2$, $A^3$, and $A^4$ can each be independently selected from the group consisting of H and a halogen, $R^1$, $R^2$, $R^4$, $R^{11}$, $R^{12}$, and $R^{13}$ each independently comprise at least one atom. In one set of embodiments, each of $A^1$, $A^2$, $A^3$, and $A^4$ can be H, Q can be methyl or ethyl, $R^1$ can be H or an aromatic group, each of $R^{11}$-$R^{13}$ can be H, $R^2$ can be methyl or ethyl, $R^4$ can be alkyl (in one embodiment, straight chain), an aromatic (in one embodiment, including at least two aromatic rings, optionally in branched configuration).

In another set of embodiments, the method includes the step of administering to a patient a therapeutically effective amount of a composition comprising a structure:

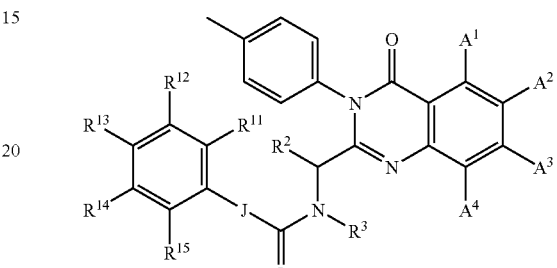

where $A^1$, $A^2$, $A^3$, and $A^4$ can each be independently selected from the group consisting of H and a halogen, J comprises a chemical bond or at least one atom, and $R^2$, $R^3$, $R^{11}$, $R^{12}$, $R^{13}$, $R^{14}$, and $R^{15}$ each independently comprise at least one atom. In one set of embodiments, each of $A^1$, $A^2$, $A^3$, and $A^4$ can be H, $R^3$ can be an cyclic group or an alkyl, which can be a straight chain alkyl, $R^2$ can be methyl or ethyl, each of $R^{11}$-$R^{15}$ can be H or methyl, J comprises a chemical bond, NHCO, or CH-phenyl.

In another set of embodiments, the method includes the step of administering to a patient a therapeutically effective amount of a composition comprising:

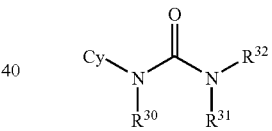

where Cy comprises a cyclic structure having at least seven members, and $R^{30}$, $R^-$, and $R^{32}$ each comprise at least one atom. In one set of embodiments, each of $R^{30}$ and $R^{31}$ can be aromatic, and $R^{32}$ can be H or halogen.

In another set of embodiments, the method includes the step of administering to a patient a therapeutically effective amount of a composition comprising a structure:

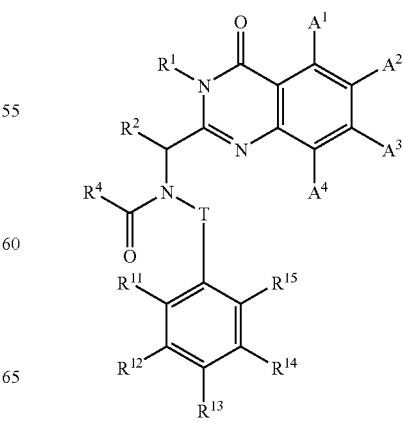

where T comprises an alkyl group having at least two carbon atoms, $A^1, A^2, A^3$, and $A^4$ can each be independently selected from the group consisting of H and a halogen, and $R^1, R^2, R^4, R^{11}, R^{12}, R^{13}, R^{14}$, and $R^{15}$ each independently comprise at least one atom. In one set of embodiments, T includes at least two carbon atoms, each of $R^{11}$-$R^{15}$ can be H or methyl, and $R^2$ can be methyl or ethyl, each of $R^1$ and $R^4$ can be aromatic, which can be halogenated, $R^1$ can be benzene or substituted benzene.

In another aspect, the invention is directed to a method of making any of the embodiments described herein. In yet another aspect, the invention is directed to a method of using any of the embodiments described herein.

In each aspect of the invention, whether composition, composition including pharmaceutical carrier, or method of making or using a composition, one set of embodiments includes any composition disclosed herein but specifically excluding any or all of the following structures, which have been demonstrated according to the screening assay described in the Examples section, not to be effective in treating characterized by aberrant expression of MUC1:

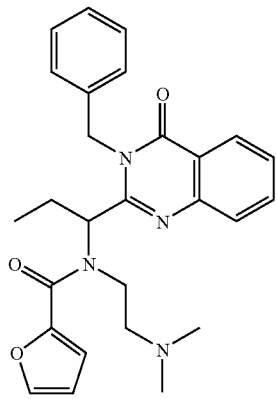

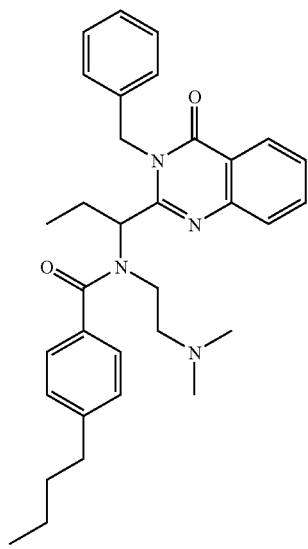

-continued

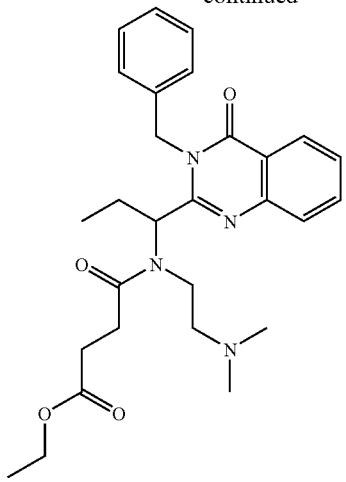

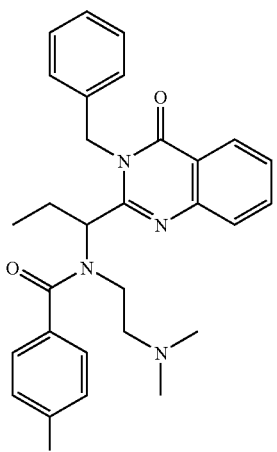

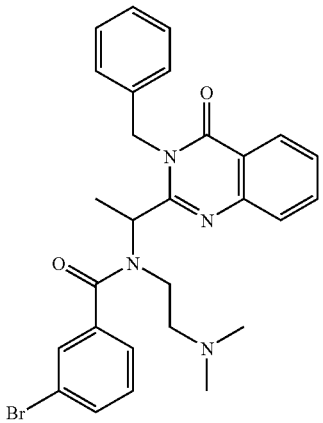

-continued

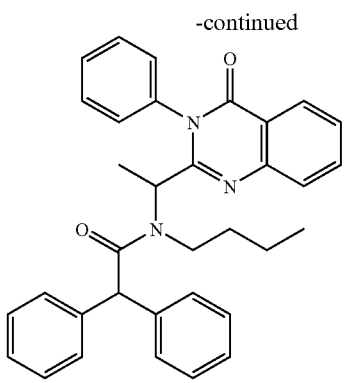

Other advantages, novel features, and objects of the invention will become apparent from the following detailed description of non-limiting embodiments of the invention when considered in conjunction with the accompanying drawings, which are schematic and which are not intended to be drawn to scale. In the figures, each identical or nearly identical component that is illustrated in various figures typically is represented by a single numeral. For purposes of clarity, not every component is labeled in every figure, nor is every component of each embodiment of the invention shown where illustration is not necessary to allow those of ordinary skill in the art to understand the invention. In cases where the present specification and a document incorporated by reference include conflicting disclosure, the present specification shall control.

BRIEF DESCRIPTION OF THE DRAWINGS

Non-limiting embodiments of the present invention will be described by way of example with reference to the accompanying drawings in which:

FIG. 2 is a graph illustrating effects that compositions of the invention have on MUC1$^+$ tumor cells in a cell proliferation assay.

DETAILED DESCRIPTION OF THE INVENTION

Figure 1:
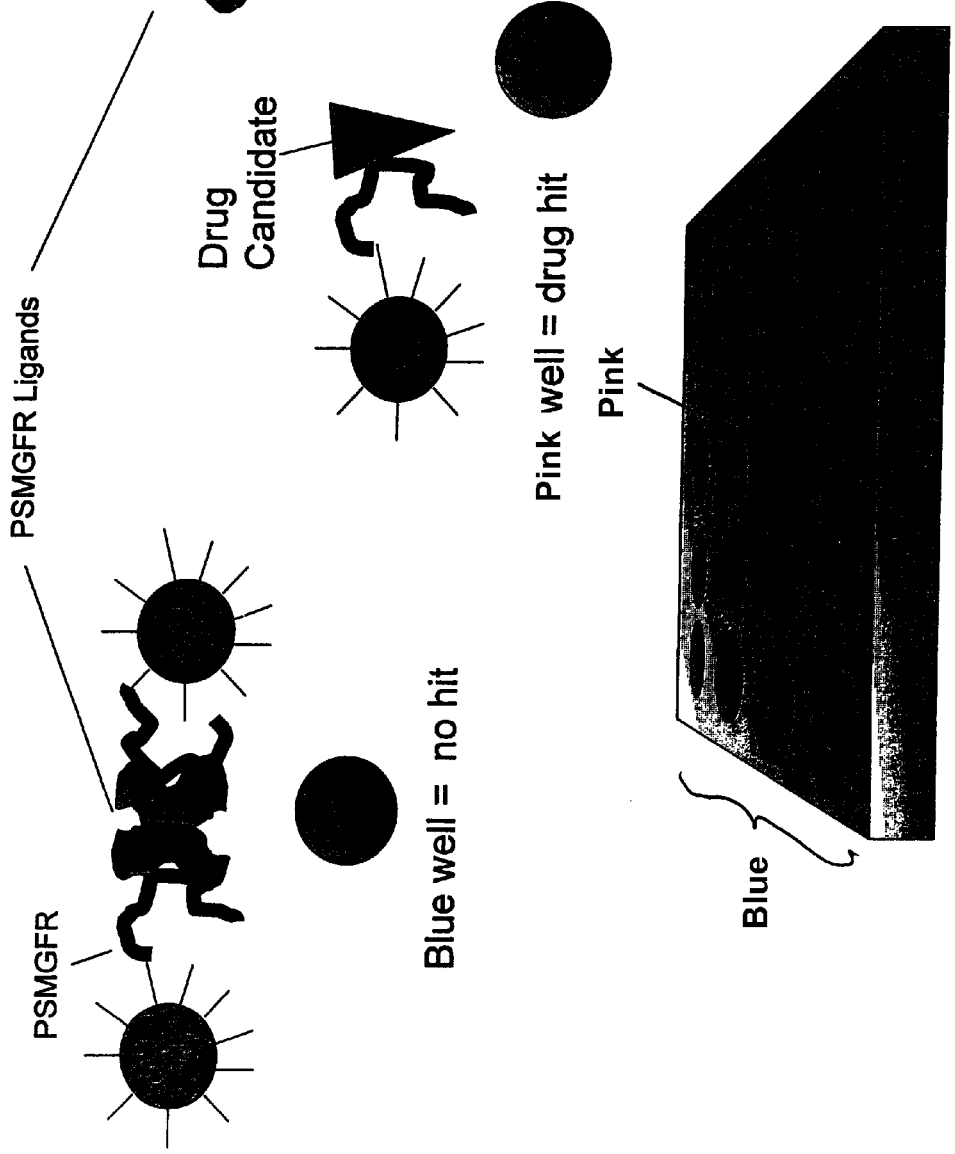
FIG. 1 illustrates a drug screening assay of a MUC1 receptor.

The present invention generally relates to compositions and methods for cancer treatment and, in particular, to compositions that are able to inhibit interactions involving the MUC1 Growth Factor Receptor or its ligands, and methods for treating patients displaying symptoms of, or susceptible to MUC1-associated cancers. The invention also relates to assays or use of such compositions for the treatment of patients susceptible to or exhibiting symptoms characteristic of cancer or tumorigenesis. Other compositions of the present invention useful for the treatment or prevention of cancer or tumorigenesis include homologs, analogs, derivatives, enantiomers or functional equivalents. In another aspect, the invention relates to the discovery of a variety of compositions (e.g., drugs) useful for inhibition of cell proliferation, including proliferation associated with tumors such as MUC1-related tumors. The compositions of the present invention can be provided in a kit including instructions for use of the composition for treatment of diseases. Assays can be performed to screen for and identify such compositions, and also for identifying which compositions are effective at various stages of the disease process.

The present invention also involves, in one aspect, methods for treating patients susceptible to or exhibiting symptoms of a tumorigenic condition or a condition where healthy receptor clustering has been disrupted.

The present invention also provides for the treatment of patients for a condition different from cancer, including conditions that can be unrelated to cancer in some embodiments of the present invention. That is, if a composition of the invention is known for treatment of a different condition, the present invention also involves use of that composition for treatment of cancer where indicated. The present invention also includes treatments where the dosage, delivery technique or vehicle, combination with other pharmaceutical compositions or lack of combination with other pharmaceutical compositions, rate of administration, timing of administration, or other factor differs from the use of the composition for treatment of the condition different from cancer.

In another set of embodiments, the invention is particularly directed to a patient population never before treated with drugs useful according to certain methods of the invention, including patients who are not suffering from or indicating susceptibility to abnormal cell proliferation, cancers or tumors, particularly MUC1-associated cancers. In other words, the treatment preferably is directed to patient populations that otherwise are free of symptoms that call for treatment with any of the drugs useful according to the invention.

International patent application serial number PCT/US01/12484, filed Apr. 12, 2001 by Bamdad et al, entitled "Treatment of Neurodegenerative Disease" (International patent publication WO 01/78709, published Oct. 25, 2001), International patent application serial number PCT/US00/01997, filed Jan. 25, 2000 by Bamdad et al., entitled "Rapid and Sensitive Detection of Aberrant Protein Aggregation in Neurodegenerative Diseases" (International patent publication WO 00/43791, published Jul. 27, 2000), and International patent application serial number PCT/US00/01504, filed Jan. 21, 2000 by Bamdad, et al., entitled "Interaction of Colloid-Immobilized Species with Species on Non-Colloidal Structures" (International patent publication WO 00/34783, published Jul. 27, 2000), all are incorporated herein by reference. Also incorporated herein by reference are the following: International patent application serial no. PCT/US01/44782, filed Nov. 27, 2001, publication WO 02/056022, pubished Jul. 18, 2002, entitled "Diagnostic Tumor Markers, Drug Screening for Tumorigenesis Inhibition, and Compositions and Methods for Treatment of Cancer", by Bamdad, et al., U.S. patent application Ser. No. 09/631,818, filed Aug. 3, 2000, entitled "Rapid and Sensitive Detection of Protein Aggregation"; U.S. provisional patent application Ser. No. 60/213,763, filed Jun. 23, 2000, entitled "Detection of Binding Species with Colloidal and Non-Colloidal Structures"; U.S. provisional patent application No. 60/248,866 by Bamdad, et al., filed Nov. 15, 2000, entitled "Detection of Binding Species with Colloidal and Non-Colloidal Structures"; U.S. provisional patent application No. 60/248,865 by Bamdad, et al., filed Nov. 15, 2000, entitled "Endostatin-Like Angiogenesis Inhibition"; U.S. Provisional Patent Application No. 60/317,302, filed Sep. 5, 2001, entitled "Compositions and Methods of Treatment of Cancer," by C. Bamdad, et al.; and U.S. Provisional Patent Application No. 60/376,732, filed May 1, 2002, entitled "Compositions and Methods of Treatment of Cancer," by C. Bamdad, et al. Also incorporated by reference is an application filed on even date herewith, entitled "Compositions and Methods of Treatment of Cancer," by C. Bamdad, et al.

The term "MUC1 Growth Factor Receptor" ("MGFR") refers to the portion of the MUC1 receptor that interacts with a ligand, such as a growth factor, to promote cell proliferation or tumorigenesis. The MGFR region is positioned close to the cell surface and may be defined by most or all of the Primary Sequence of the MUC1 Growth Factor Receptor ("PSMGFR"). The results of the present invention are consistent with a mechanism in which the MGFR region is accessible to the ligand upon MUC1 cleavage, at a site associated with tumorigenesis that causes release of the IBR from the cell.

The term "Interchain Binding Region" ("IBR") refers to the portion of the MUC1 receptor that is able to bind strongly with homologous or complementary regions of other MUC1 receptors, giving MUC1 the ability to aggregate (i.e., self-aggregate) with other MUC1 receptors, for example, via the IBRs of the respective receptors. This self-aggregation property of certain MUC1 receptors may contribute to the clustering of some MUC1 receptors which has previously been observed in some healthy cells.

The term "cleaved IBR" refers to an IBR (or a portion thereof) that has been released, due to a cleavage event, from a MGFR molecule, leaving behind a segment that remains attached to the cell surface. The release of the cleaved portion of the IBR may be due to enzymatic cleavage or other cleavage events. As used herein, an IBR "at the surface of a cell," refers to an IBR attached to a cell surface receptor or a portion thereof that has not been shed or cleaved. The cleaved IBR of interest is a "disease-associated cleavage," i.e., a type of cleavage that can result in tumorigenesis or cancer.

The term "Constant Region" ("CR") is any non-repeating sequence of MUC1 that exists in a 1:1 ratio with the IBR and forms part of the portion of MUC that is shed upon cleavage in healthy or tumorigenic cells.

The term "repeats" is given its normal meaning in the art.

The term "Primary Sequence of the MUC1 Growth Factor Receptor" (PSMGFR) is a peptide sequence (GTINVHDVETQFNQYKTEAASPYNLTISDVSVSDVPFPFSAQSGA) that defines most or all of the MGFR.

The term "Extended Sequence of the MUC1 Growth Factor Receptor" (ESMGFR) is a peptide sequence (VQLTLAFREGTINVHDVETQFNQYKTEAASPYNLTISDVSVSDVPFPF) that defines all of PSMGFR plus 9 amino acids of the proximal end of PSIBR.

PSIBR is a peptide sequence (GFLGLSNIKFRPGSVVVQLTLAFRE) that defines most or all of the IBR.

The term "separation" means physical separation from a cell, e.g., a situation in which a portion of MUC1 that was immobilized with respect to a cell is no longer immobilized with respect to that cell. For example, in the case of cleavage of a portion of MUC1, the portion that is cleaved is "separated" if it is free to migrate away from the cell and thereafter may be detected, for example, in a bodily fluid, or immobilized at a location remote from the cell from which it was cleaved such as another cell, a lymph node, etc.

The term "aggregate" (noun) refers to a plurality of cell surface receptors or fragments thereof (e.g., MUC1), immobilized with respect to each other with or without an intermediate auxiliary to the host system. This includes self-aggregation of healthy receptors at a cell surface; self-aggregation of cleaved receptors or fragments bound to each other; cleaved receptors or fragments bound to receptors or fragments attached to a cell surface; and receptors or fragments, whether attached to a cell or cleaved, immobilized with respect to each other via an intermediate auxiliary to the host. "Intermediate auxiliary to the host system" includes a synthetic species such as a polymer, dendrimer, etc., or a naturally-occurring species, which is not simply naturally present in the host system but is added to the host system from a source external to the host system. This excludes aggregation that is the result of an intermediate naturally present in the host system such as a growth factor that can cause disease-associated aggregation. "Aggregate" (verb) or "aggregation" means the process of forming an aggregate (noun).

"Colloid," as used herein, means nanoparticle, i.e. a very small, self-suspendable particles including inorganic, polymeric, and metal particles. Typically, colloid particles are of less than 250 nm cross section in any dimension, more typically less than 150 or 100 nm cross section in any dimension, and preferably 10-30 nm, and can be metal (for example, gold colloid particles), non-metal, crystalline or amorphous. As used herein this term includes the definition commonly used in the field of biochemistry.

The term "cancer," as used herein, may include, but is not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer.

The term "cancer treatment" as described herein, may include, but is not limited to, chemotherapy, radiotherapy, adjuvant therapy, or any combination of the aforementioned methods. Aspects of treatment that may vary include, but are not limited to dosages, timing of administration or duration or therapy; and may or may not be combined with other treatments, which may also vary in dosage, timing, or duration. Another treatment for cancer is surgery, which can be utilized either alone or in combination with any of the aforementioned treatment methods. One of ordinary skill in the medical arts may determine an appropriate treatment for a patient.

An "agent for prevention of cancer or tumorigenesis" refers to any agent able to counteract any process associated with cancer or tumorigenesis, for example, as described herein. For example, an agent that interacts with (e.g., binds to) MGFR is able to reduce or prevent interaction of MGFR with an agent that promotes tumorigenesis by its interaction with MGFR.

An "agent that reduces cleavage of a cell surface receptor interchain binding region," as used herein, is any composition that prevents or reduces cleavage of the MUC1 receptor between the MGFR and the IBR that would otherwise occur in the absence of the agent. Compositions disclosed herein may function by reducing cleavage of cell surface receptor interchain binding regions, or may modify MGFR regions. Cleavage of the receptor between the MGFR and the IBR may be caused by activity of one or more enzymes that are membrane-associated or soluble. Some of these enzymes are directly responsible for cleavage of the receptor. Other enzymes can affect cleavage, for example, by modifying MUC1 with moieties such as sugar groups or phosphates able to mask or alter a recognition epitope associated with the cleavage site. Other enzymes may promote cleavage at a particular location, for example, by modifying MUC1 with moieties such as sugar groups or phosphates able to create a recognition motif for cleavage associated with that location. One example way to select agents able to reduce cleavage of a cell surface receptor IBR is to first identify enzymes that affect cleavage such as those described above, then test or screen various agents and their analogs for their ability to alter the activity of those enzymes. Another example way is to test agents known to affect the activity of similar enzymes (e.g., from the same family or having a homologous structure) for their ability to alter the associated site of cleavage of MUC1, and to similarly test analogs of those agents. As another example, agents may be screened in a cell-free assay containing the enzyme and MUC1 receptors, and the rate or position of cleavage may be determined and measured by any suitable technique, for example, by antibody probing, polymerase chain reaction ("PCR") or the like. As another example, without first identifying enzymes able to affect MUC1, various agents may be screened against cells that present MUC1 for the agents' ability to alter cleavage site or the rate of cleavage of MUC1. For example, various agents may be screened in an assay containing whole cells that present MUC1; the aggregation potential of the cell supernatant can then be measured as an indication of the amount of IBR remaining attached to the cleaved portion of MUC1, i.e., the degree of cleavage between MGFR and IBR. In another example technique, various agents may be screened in an assay containing whole cells that present MUC1 where the cell supernatant is first removed, and the cellular residuals tested for accessibility of the MGFR portion, e.g., by using a labeled antibody to the MGFR. Various agents suitable for use with the invention can be chosen and identified by any suitable technique, for example, the agents may be identified from commercially available sources such as molecular libraries, or rationally designed based on known agents having the same functional capacity and tested for activity using the screening assays.

An "agent that reduces cleavage of the MUC1 receptor" is any composition able to prevent or reduce cleavage of the MUC1 receptor at any location. Such an agent may be used to treat a subject having cancer or at risk for developing cancer, because if cleavage of the MUC1 receptor is prevented, then the accessibility of the MGFR, a functional receptor associated with cancer, is reduced or prevented. Such agents may be selected by any suitable technique. For example, the agents may be selected by exposing cells to a candidate agent and determining, in the supernatant, the amount of cleaved MUC1 receptor present, relative to a control.

A "subject" or a "patient," as used herein, refers to any mammal (preferably, a human), and preferably a mammal that may be susceptible to tumorigenesis or cancer associated with the aberrant expression of MUC1. Examples include a human, a non-human primate, a cow, a horse, a pig, a sheep, a goat, a dog, a cat or a rodent such as a mouse, a rat, a hamster, or a guinea pig. Generally, or course, the invention is directed toward use with humans.

A "sample," as used herein, is any cell, body tissue, or body fluid sample obtained from a subject. Preferred are body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

As used herein, the term "hedgehog" refers to members of the hedgehog family of singling molecules that mediate certain patterning processes during development. For example, member of the hedgehog family control left-right assymmetry, polarity in the central nervous system, organogenesis, and chondrogenesis. The hedgehog gene is involved in the regulation of neurotissues, bone and cartilage formation and repair, regulation of spermatogenesis, regulation of smooth muscle, regulation of lung, liver and other organs arising from the primitive gut, regulation of hematopoietic function, or regulation of skin and hair growth. The present invention is directed toward cancers arising from aberrant expression of the MUC1, and are not directed to the inhibition of hedgehog, for instance, by targeting the primary pathway of hedgehog. The compounds of the present invention are not currently known to inhibit hedgehog.

Any additional definitions necessary for understanding the invention can be taken from International patent publication no. WO 02/056022, referenced above.

The present invention generally involves compositions related to cancers and methods of treatment of cancers characterized by the aberrant expression of a class of cell surface receptors characterized by interchain binding regions. One such set of cancers are those cancers characterized by the aberrant expression of MUC1. Much of the description of the invention herein involves cells that aberrantly express MUC1. It is to be understood that in these instances the description is to be considered exemplary, and that the principles of the invention apply to other cell surface receptors that function by a similar mechanism. With the disclosure herein, those of ordinary skill in the art will readily be able to identify other cell surface receptors that function by this or a similar mechanism, and to apply the invention to those cancers characterized by aberrant expression of those receptors. The invention is based on a novel mechanism involving aberrant expression of cell surface receptors, exemplified by MUC1, which was elucidated by the inventors.

The cell surface receptor MUC1, which is a tumor marker, is aberrantly expressed in many human cancers, including about 80% or 90% of breast tumors, and in a significant percentage of other human tumors, such as prostate, lung, ovarian, colorectal, and perhaps brain cancer. Extracellular portions of the MUC1 receptor may be cleaved or "shed" by at least one enzyme, and may be released into the bloodstream in some cases. Cleavage of the MUC1 receptor may occur at more than one site, and the site of cleavage may be associated with a propensity for cancer. On the surface of tumor cells, the pattern of expression of MUC1 may be altered from that on healthy cells. In a healthy cell such as a cell in an epithelium, the MUC1 receptors often clustered at the apical border of the cell. In contrast, in a tumor cell, the receptors may be expressed or overexpressed, and distributed relatively homogeneously over the surface of the cell. One aspect of the present invention features the discovery that a specific region of MUC1, i.e., the IBR, is able to bind strongly to identical or homologous regions of other MUC1 receptors. That is, some MUC1 receptors have the ability to aggregate (i.e., self-aggregate) with other MUC1 receptors via the IBR of the respective receptors. This self-aggregation property of certain MUC1 receptors may contribute to the clustering of some MUC1 receptors which has previously been observed in some healthy cells. The discovery that the IBR portion of the MUC1 receptor self-aggregates is consistent with the following mechanistic model for which the inventors present supporting evidence. In this mechanistic model, (1) receptor clustering is associated with the healthy state, as aggregated IBR portions may block access of ligands such as growth factors to the extracellular portions of the MUC1 receptor acting as functional receptors; clustering may also block access of the intracellular regions to signaling ligands; and (2) if the MUC1 receptor is cleaved at a position that causes the release of IBR, the critical force that keeps the receptors clustered may be lost and the receptors may then be free to migrate within the cell or cell membrane, or interact with modifying enzymes or secreted ligands such as growth factors or other cell surface receptors; these interactions could involve a new multimerization state, such as dimerization, that may trigger a cell proliferation signaling cascade in some cases.

This mechanistic model suggests that in a subject with a MUC1-dependent tumor, or who is prone to developing such a tumor, the portion of the MUC1 receptor that is shed contains the IBR region of the receptor, leaving the MGFR portion of the receptor accessible for interactions with various ligands or growth factors. One diagnostic tool thus would consist of detecting the IBR region of the portion of the MUC1 receptor which is shed.

This model is also consistent with a mechanism whereby the portion of the MUC1 receptor that remains attached to the cell surface after shedding of the IBR region, the MGFR (MUC1 Growth Factor Receptor), is able to function as a receptor for ligands that can trigger cell proliferation. This mechanism is demonstrated herein with a showing that (1) an interaction between a ligand and this portion of the MUC1 receptor (MGFR) triggers cell proliferation in some cases; and (2) blocking the interaction of this portion of the MUC1 receptor with a ligand is able to block cell proliferation. When tumor cell lines in which the MUC1 receptor is homogeneously expressed across the entire cell surface are treated with an antibody raised against the MGFR portion of the MUC1 receptor, the rate of cell proliferation can be greatly enhanced. Binding of a ligand to the MGFR portion of the MUC1 receptor may allow the receptor to dimerize. Thus, one effective therapeutic strategy may be to block the MGFR portion of the receptor, for example, with a monomeric composition, which may prevent dimerization or subsequent signaling cascades. For example, a single chain, or monovalent, antibody raised against the MGFR portion of the MUC1 receptor may be able to function as an anti-cancer therapeutic.

MUC1 comprises several regions termed herein as follows, recited in an order starting from the region closest to the cell surface and progressing away from the cell. In at least one U.S. provisional patent application ("earlier application(s)"), at least one region of MUC1 was defined differently. It is to be understood that the following definition supercedes. Those of ordinary skill in the art will understand the invention in all its aspects from the description of portions of MUC1 referred to differently in the earlier application(s) and in the current application and the relation of the earlier application(s) to this application. The PSMGFR was referred to in the earlier application(s) as an FLR region or peptide. The PSIBR was referred to in the earlier application(s) as a CM region or peptide.

One aspect of the invention is directed to a method for treating a subject diagnosed or at risk of cancer or tumor characterized by the aberrant expression of MUC1. The treatments of the present invention involve the use of compositions or "agents" as described herein. That is, one aspect of the invention involves a series of compositions or agents useful for treatment of cancer or tumor characterized by the aberrant expression of MUC1. These compositions may also be packaged in kits, optionally including instructions for use of the composition for the treatment of such conditions. These and other embodiments of the invention may also involve promotion of the treatment of cancer or tumor according to any of the techniques and compositions and combinations of compositions described herein.

One aspect of the invention provides a pharmaceutical preparation comprising a composition comprising any of compositions shown below (numbered 1-51), optionally with a pharmaceutically active carrier:

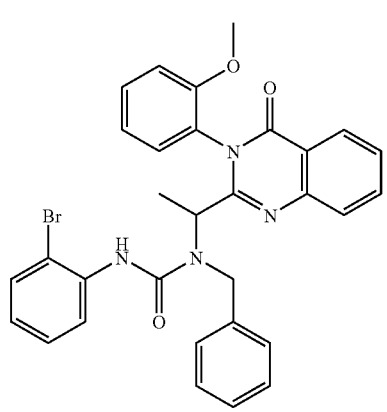

1

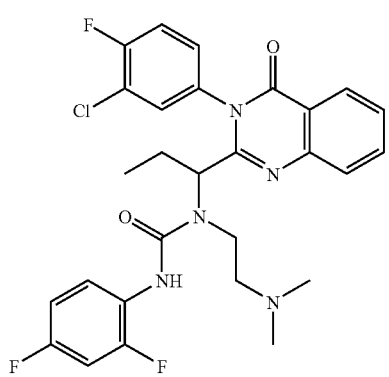

2

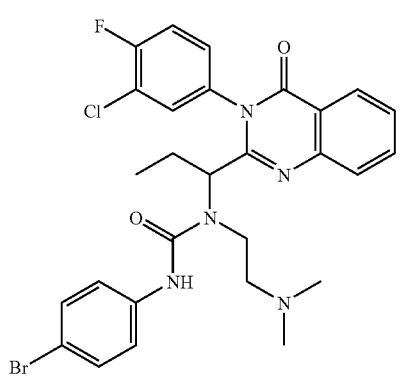

3

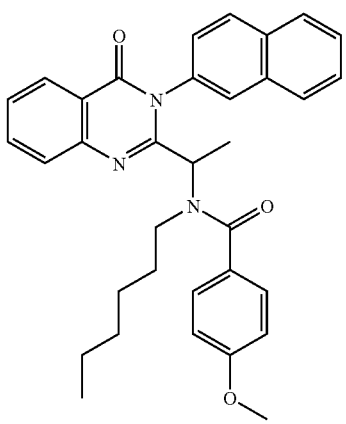
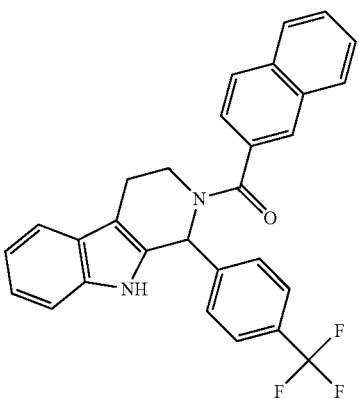
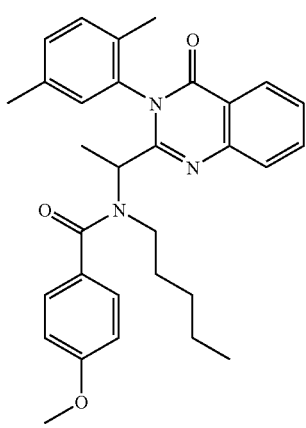
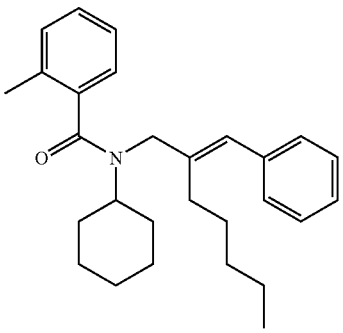
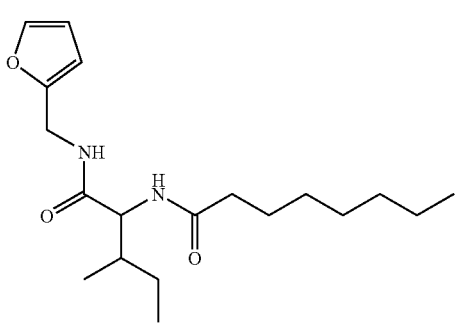
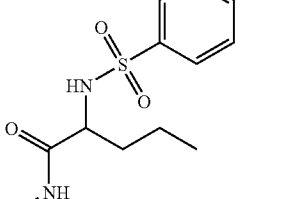
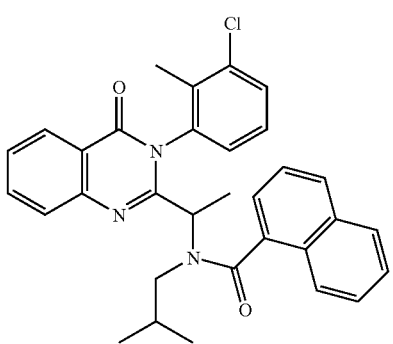
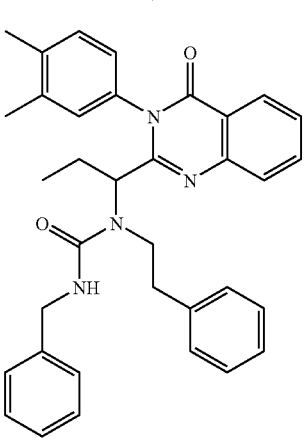

12
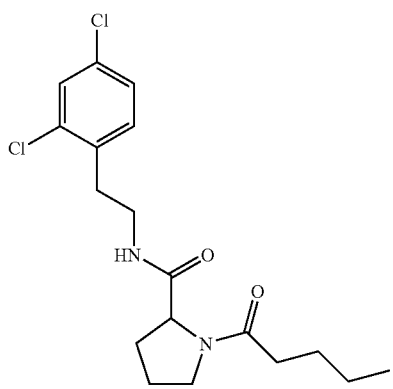
13
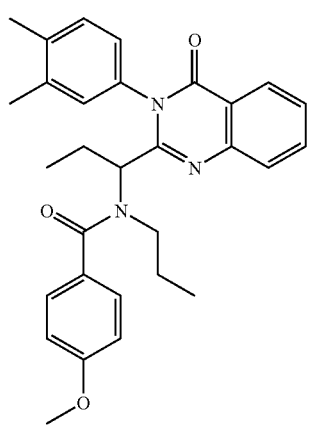
14
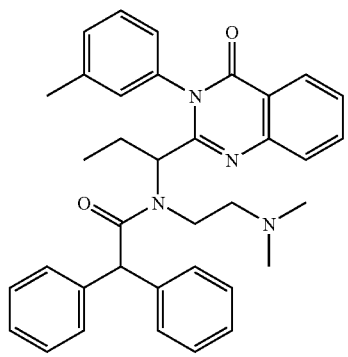
15
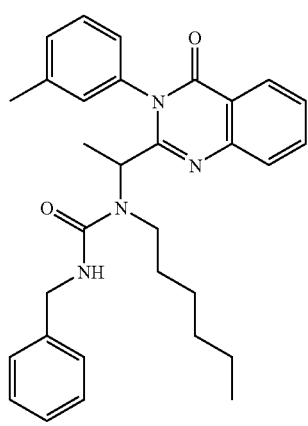
16
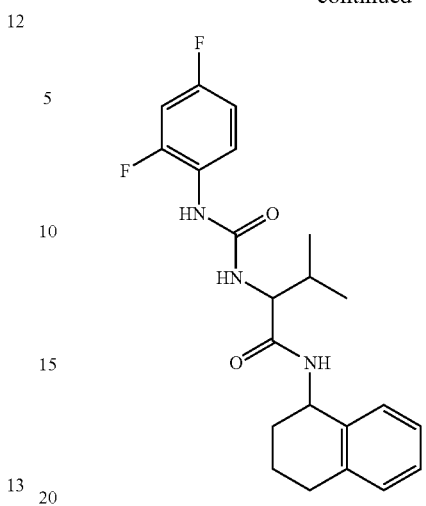
17
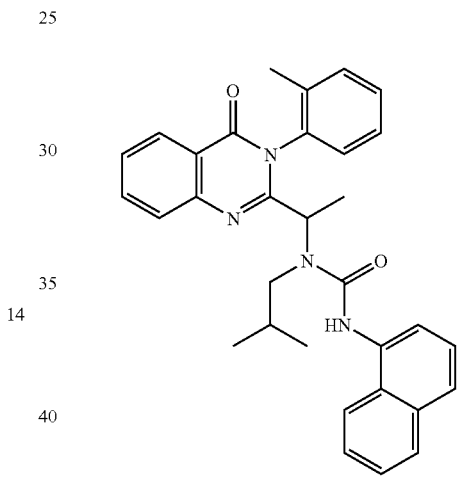
18
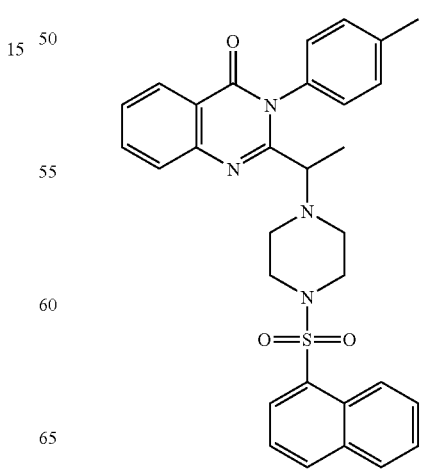

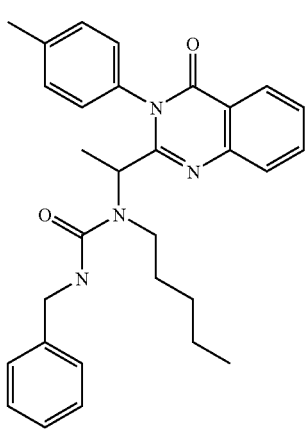
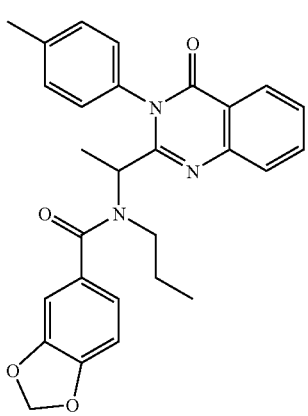
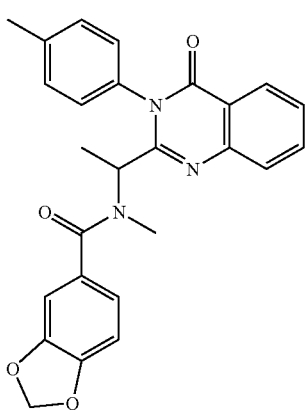
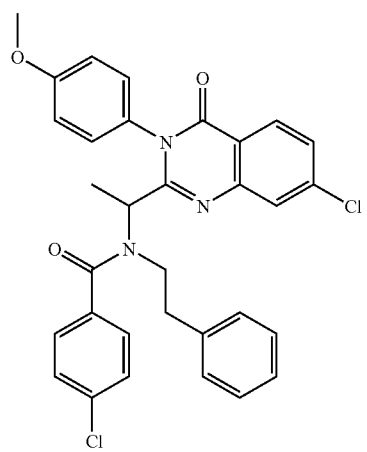
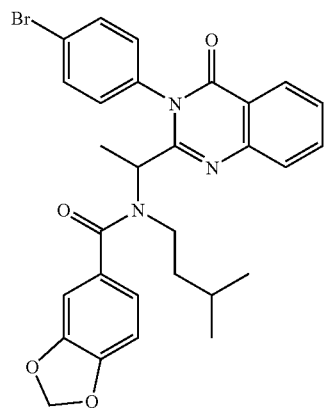
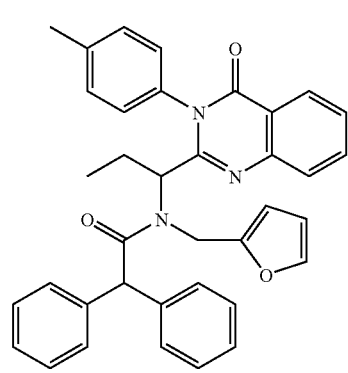
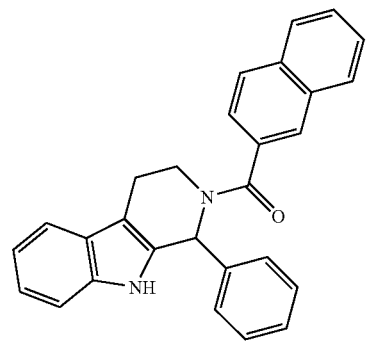

26
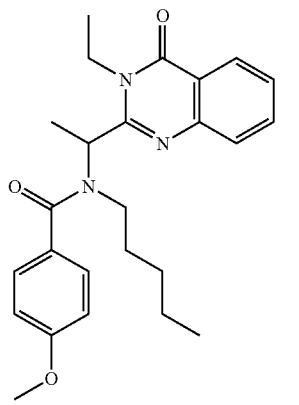
27
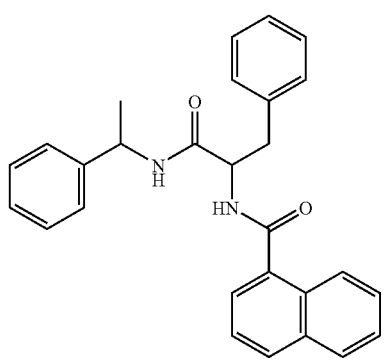
28
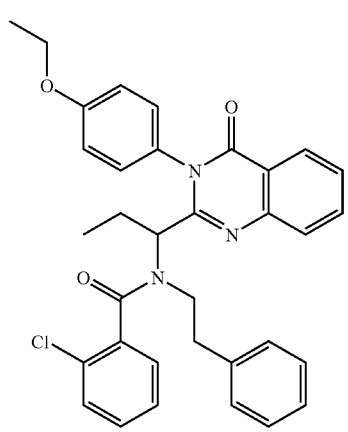
29
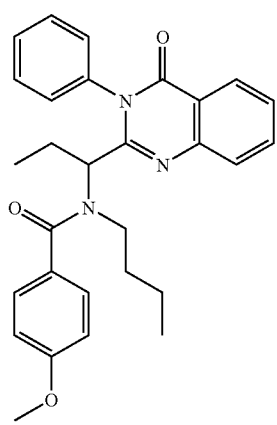
30
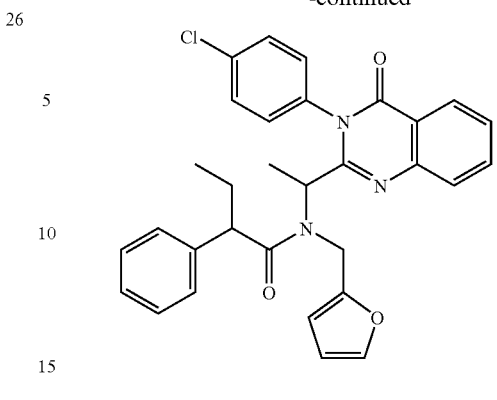
31
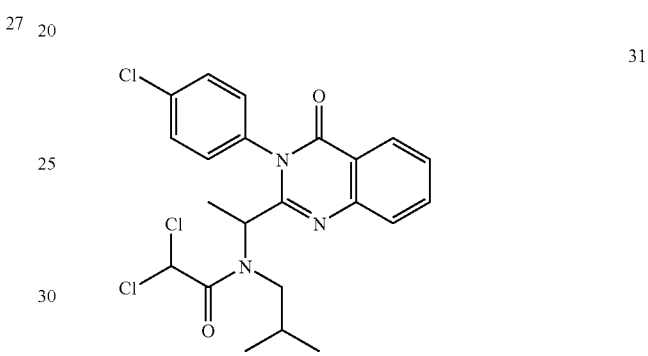
32
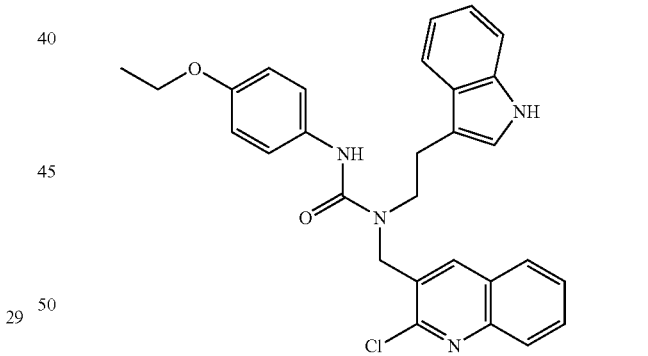
33
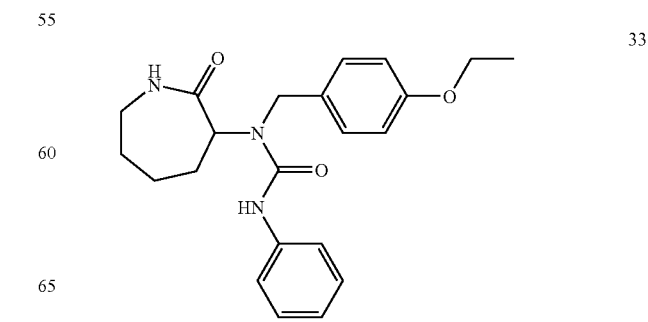

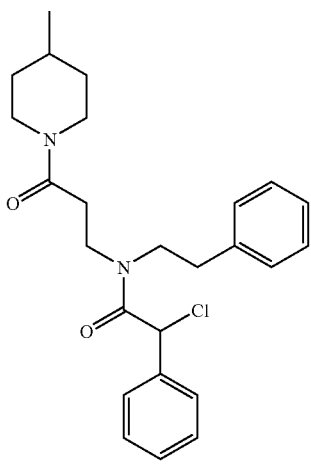
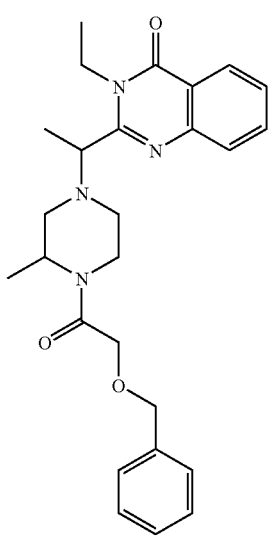
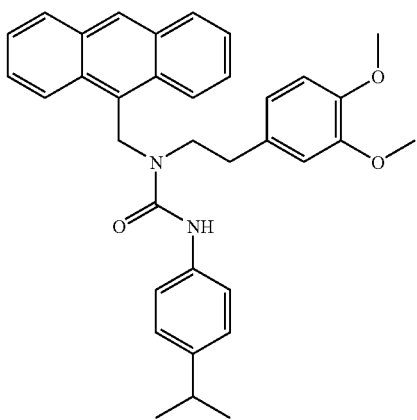
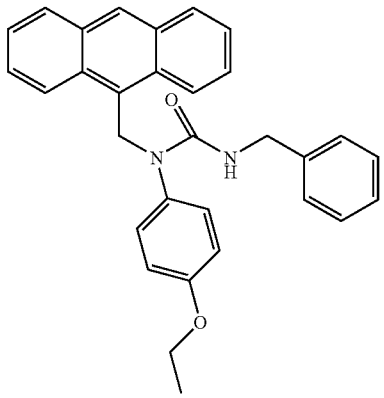
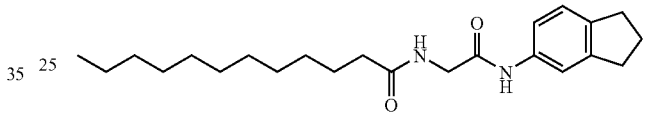
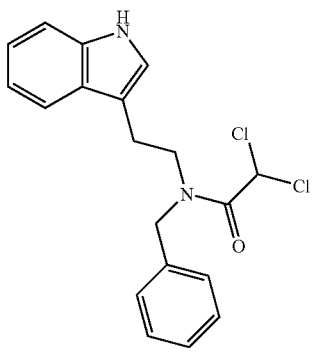
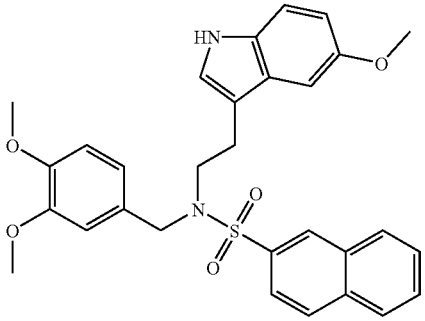
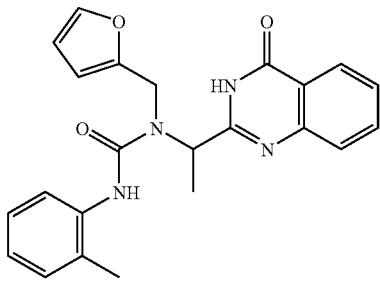

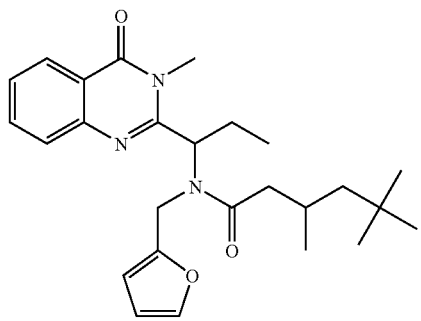
42
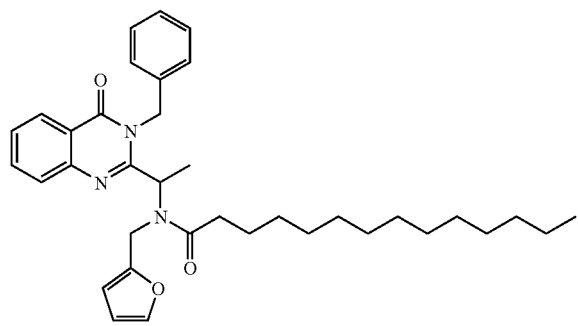
43
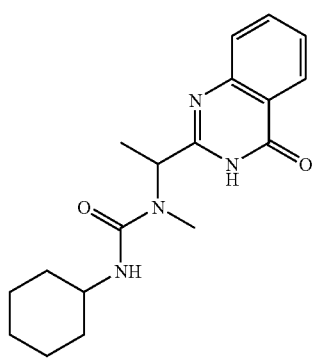
44
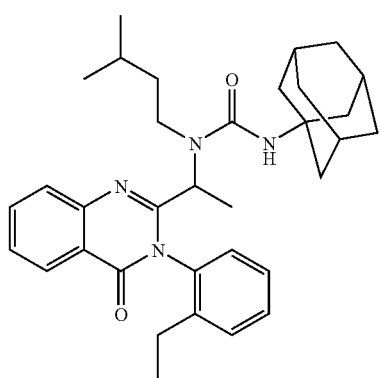
45
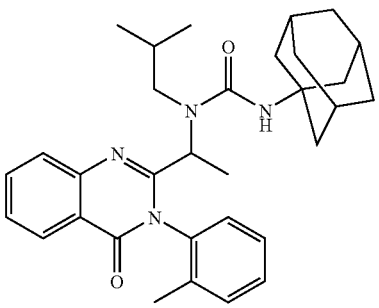
46
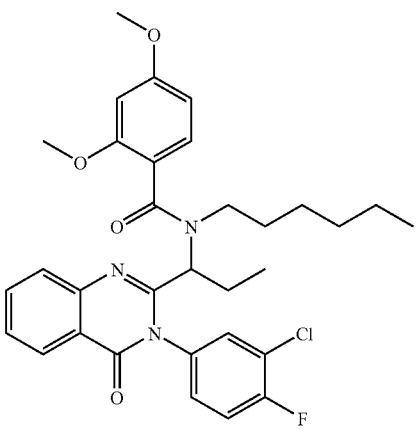
47
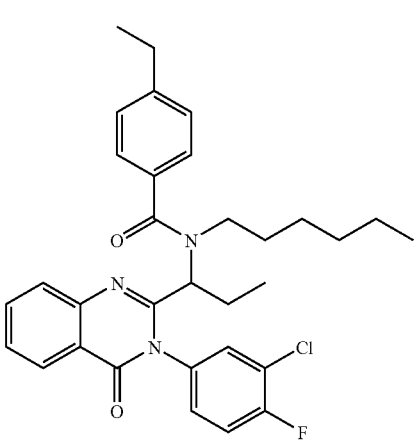
48
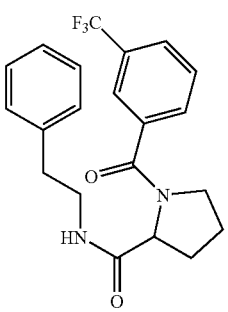
49

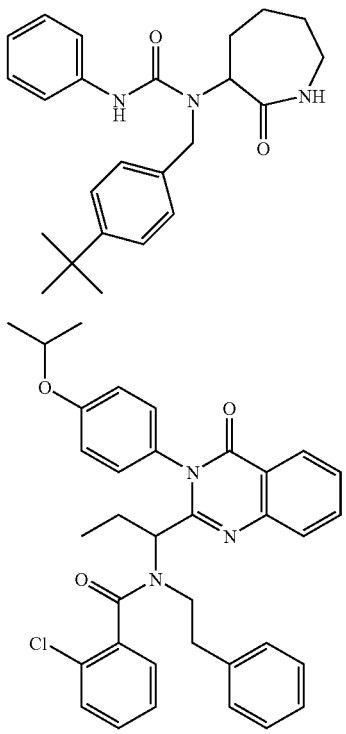

50

51

In one embodiment, the composition comprises homologs, analogs, derivatives, enantiomers and functionally equivalent compositions thereof of compositions 1-51. Another aspect of the present invention provides any of the above-mentioned compositions as being useful for the treatment of cancer and particularly MUC1-associated cancers. In one embodiment, particularly preferred compositions are compositions 19, 21, 37, 41, 43 and 45-51.

In one aspect, the invention is defined, at least in part, by compositions having certain structures, as further described below. In these structures, the term "chemical bond" refers to any type of chemical bond, for example, a covalent bond, an ionic bond, a hydrogen bond, a van der Waals bond, a metal ligand bond, a dative bond, a hydrophobic interaction, or the like. It is to be understood that all compositions are useful for any of the methods of treatment described herein.

In these structures, atoms able to form at least three covalent bonds include those atoms of the carbon family (e.g., carbon, silicon, or germanium), the nitrogen family (e.g., nitrogen, phosphorus, or arsenic), or the boron family (e.g., boron, aluminum, or gallium). In some embodiments, the atoms able to form at least three covalent bonds found within structures of the invention are carbon, nitrogen, silicon, and phosphorus, and in certain embodiments, the atoms are carbon and nitrogen.

The term "halogen," or equivalently, "halogen atom," is given its ordinary meaning as used in the field of chemistry. The halogens include fluorine, chlorine, bromine, iodine, and astatine. Preferably, the halogen atoms used in the present invention include one or more of fluorine, chlorine, bromine, or iodine. In certain embodiments of the invention, the halogen atoms found within the structure are fluorine, chlorine, and bromine; fluorine and chlorine; chlorine and bromine; or a single type of halogen atom.

As used herein, a "saturated" bond is given its ordinary meaning as used in the field of chemistry. A saturated moiety generally does not contain any double, triple, or higher order chemical bonds in its structure. The saturated moiety can contain any number or types of atoms (e.g., oxygen, carbon, nitrogen, hydrogen, or halogen atoms) in any configuration, so long as the moiety contains only single bonds between the atoms. For example, the saturated moiety may be an aliphatic structure or a cyclic structure. A saturated moiety may be connected to a parent structure at one or more points. Examples of saturated moieties include:

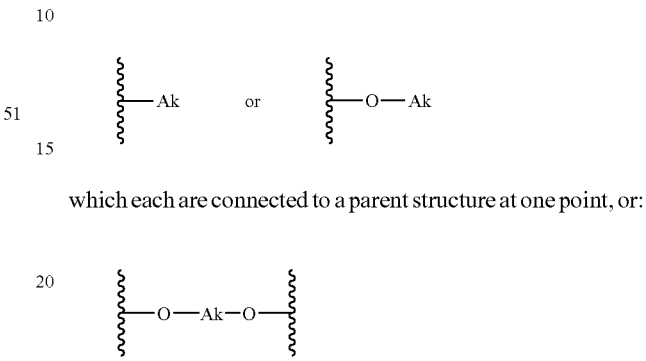

which each are connected to a parent structure at one point, or:

which is connected to a parent structure at more than one point (in this example, using ether linkages). In these structures, "Ak" refers to an alkyl group, as described below. As one example, the alkyl group in these structures may have one, two, three, or four carbon atoms, and may be straight-chained or branched, as long as no double or triple bonds are present. The alkyl group may also include only hydrogen atoms, or include halogen atoms as well.

Conversely, an "unsaturated" moiety is a moiety that contains at least one higher-order chemical bond within its structure, i.e., at least one double bond or triple bond between two atoms within its structure. The unsaturated moiety may contain, in some cases, more than one double and/or triple bond within its structure, for example, as in an alkadiene or an alkenyne.

As used herein, an "alkyl" is given its ordinary meaning as used in the field of organic chemistry. Alkyl or aliphatic groups typically contains any number of carbon atoms, for example, between 1 and 20 carbon atoms, between 1 and 15 carbon atoms, between 1 and 10 carbon atoms, or between 1 and 5 carbon atoms. In some embodiments, the alkyl group will contain at least 1 carbon atom, at least 2 carbon atoms, at least 3 carbon atoms, at least 4 carbon atoms, at least 5 carbon atoms, at least 6 carbon atoms, at least 7 carbon atoms, or at least 8 carbon atoms. Typically, an alkyl group is a non-cyclic structure. In certain embodiments, the alkyl group is a methyl group or an ethyl group.

The carbon atoms may be arranged in any configuration within the alkyl moiety, for example, as a straight chain (i.e., a n-alkyl such as methyl, ethyl, propyl, butyl, pentyl, hexyl, heptyl, octyl, nonyl, decyl, or undecyl) or a branched chain, for example, a t-butyl group, or an isoalkyl group such as isopropyl, isobutyl, ispentanyl, or isohexanyl. The alkyl moiety may contain none or any number of double or triple bonds within its structure, for example, as in an alkene, an alkyne, an alkadiene, an alkadiyne, an alkenyne, etc.

The alkyl group may contain any number of substituents. For example, the alkyl group may contain a halogen, an alkoxy (e.g., a methoxy, an ethoxy, a propoxy, an isopropoxy, a butoxy, a pentoxy, or the like), an amine (e.g., a primary, secondary, or tertiary amine, for example, an dimethylamine ethyl group), or a hydroxide as a substituent. As one example, if the alkyl group is a methyl group, then the methyl group may be substituted to form, for instance, a halogenated methyl group such as chloromethyl, bromomethyl, or iodomethyl. In some embodiments of the invention, more than one substituent may be present. For example, the alkyl group may have two or more halogen atoms (for example, two chlorine atoms, or a chlorine and a bromine atom), a halogen and an alkoxy group, or the like.

In some embodiments of the invention, the alkyl group may also contain one or more heteroatoms substituted within the alkyl group, such as a nitrogen atom (e.g., as in an amine such as a primary, secondary, or tertiary amine) or an oxygen atom (as in an ether moiety). However, in other embodiments of the invention, the main chain of the alkyl group is free of heteroatoms and includes carbon atoms. As used herein, the term "heteroatoms" refers to atoms that can replace carbon atoms within an alkyl group without affecting the connectivity of the alkyl group; these typically include oxygen and nitrogen atoms. Halogen atoms and hydrogen atoms are not considered to be heteroatoms; for example, a chlorine atom can replace a hydrogen atom within an alkyl group without affecting the connectivity of the alkyl group As used herein, a "non-heteroatom alkyl group" is an alkyl group which does not contain any atoms at the carbon positions other than carbon. Some structures are defined as being free of non-terminal heteroatoms. As used herein, a "non-terminal" atom is an atom within a structure that is connected to at least two different atoms having a valency greater than 1 (e.g., the atom is connected to two non-hydrogen and non-halogen atoms). For example, the oxygen in —$CH_2$—OH and the nitrogen atom in —$CH_2$—$NH_2$ are not connected to two different atoms having a valency greater than 1, and thus are not non-terminal heteroatoms.

Similarly, a "cyclic" structure, as used herein, is given its ordinary definition in the field of organic chemistry, i.e., a structure that contains at least one ring of atoms, and may contain more than one ring of atoms. In other words, a cyclic structure has at least one chain of atoms that does not have a terminal end. The chain may have, for example, three, four, five, six, seven, or more atoms arranged to form a ring. The atoms within the chain may be carbon atoms, nitrogen atoms, oxygen atoms, silicon atoms, or any other atom that is able to bond to at least two different atoms.

In some embodiments of the invention, one or more substituents may be present on the cyclic structure. The substituents may be any substituent, as previously described in connection with alkyl moieties, for example, a halogen, an alkoxy, an amine, a hydroxide, or the like. In some embodiments, the substituents may also be alkyl groups, as previously described, for example, a methyl group, an ethyl group, a propyl group, and the like.

The cyclic structure may have one or more heteroatoms in some embodiments. For example, the cyclic structure may include a cyclohexane or a cyclopentane ring having one or more heteroatoms, such as:

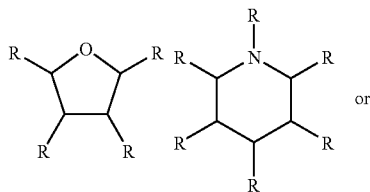

-continued

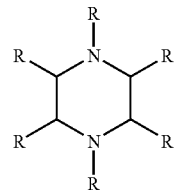

where the R's indicate the presence of additional atoms or substituents. The atoms substituted within the cyclohexane ring are able to form at least three covalent bonds, and, if able to form four covalent bonds, the fourth covalent bond may be attached to any atom.

The cyclic structure may be a saturated cyclic structure (such as a cyclohexyl or a cyclopentyl structure), or an unsaturated cyclic structure (such as a cyclohexenyl structure or an aromatic structure). Examples of aromatic structures, include, for instance, phenyl, naphthalenyl, anthacenyl, tolyl, pyridinyl, furanyl, pyrrolyl, and the like. A "nonaromatic cyclic structure" is a structure in which aromaticity of the cyclic structure is not present (for example, as in a saturated cyclic structure, a cycloalkenyl moiety, etc.)

In one set of embodiments, the aromatic structure includes a benzene ring. If substituents are present on the benzene ring (as previously discussed, for example, a halogen atom, a methyl group, a methoxy group, a trifluoromethyl group, etc.), they may be located in any position, i.e., in any ortho, meta, or para position, relative to the point of attachment of the benzene ring. If more than one substituent is present, then the substituents may be located at any available point within the benzene ring. For example, if there are two substituents, they may be located in the ortho and meta positions (i.e., in the 2, 3 or 2, 5 positions), the ortho and para positions, in the two ortho positions, in the two meta positions, or in the meta and para positions.

In one set of embodiments, the aromatic group is a non-substituted aromatic group, for example, a phenyl or a naphthalenyl group. In another set of embodiments, the aromatic structure is a halophenyl group or a dihalophenyl group, for example, 3-chloro-4-flurophenyl; o-, m-, or p-chlorophenyl; 2,4-difluorophenyl; or o-, m-, or p-bromophenyl. In another set of embodiments, the aromatic structure is a methylphenyl or a dimethyl phenyl group, for example, o-, m-, or p-methylphenyl; 2,3-dimethylphenyl; 2,4-dimethylphenyl; 2,5-dimethylphenyl. In another set of embodiments, the aromatic group is an alkylphenyl group, such as o-, m-, or p-methylphenyl; o-, m-, or p-ethylphenyl; 2-phenylethyl, or benzyl. In another set of embodiments, the aromatic structure is a halomethylphenyl group, such as 3-chloro-2-methylphenyl. In another set of embodiments, the aromatic structure is an alkoxyphenyl or a dialkoxyphenyl group, for example, o-, m-, or p-isopropoxyphenyl; o-, m-, or p-methoxyphenyl; o-, m-, or p-ethoxyphenyl; or 2,4-dimethoxyphenyl. In one set of embodiments, the aromatic group is fused with another ring of atoms. The second ring may be aromatic or nonaromatic. Examples include:

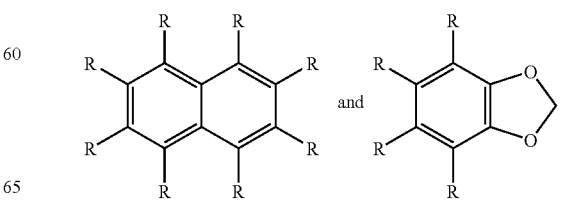

where the R's indicate the presence of additional atoms or substituents.

If the cyclic structure has more than one ring of atoms, the rings may be distributed in any manner within the moiety. For example, the two rings may not share a common atom, share only one common atom (e.g., as in a spiro-structure), or share more than one atom, as in a bicyclic structure or a propellane structure. If the two rings share at least one common chemical bond between two atoms, then the rings may be considered to be "fused."

One example of a fused ring system is a structure:

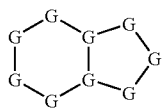

where a five member ring is fused to a six member ring in a bicyclic arrangement, and G represents atoms each having at least three covalent bonds, as previously discussed. In some embodiments, one or both rings may be aromatic. As one example, a single nitrogen substitution onto the five-member ring, when both rings are aromatic, can result in an indole moiety, for example:

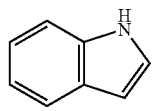

Additionally, other substituents or cyclic rings may be substituted onto the structure as well, for example, a cyclohexyl moiety.

If several rings are jointly fused to each other, then the rings may be considered to be "multifused." One example of a multifused compound is an adamantane structure:

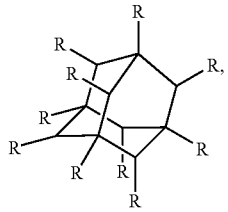

where the R's indicate the presence of additional atoms or substituents.

As used herein, when two cyclic groups are in a "branched configuration," the two cyclic groups are on different branches of a common moiety. In other words, the two cyclic groups are not serially arranged relative to each other. That is, removal of either of the cyclic structures within the moiety does not automatically cause the other cyclic structure to be disconnected from the rest of the moiety. One example of this is illustrated by a diphenylmethyl moiety:

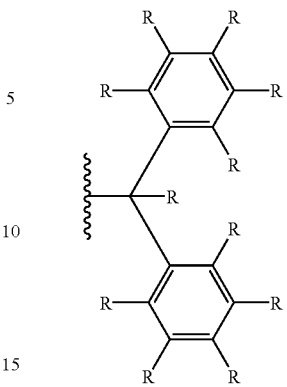

where the R's indicate the presence of additional atoms or substituents.

In one set of embodiments, the composition includes a substituted urea moiety. The substituted urea moiety includes at least one cyclic structure having at least seven members. In some cases, the cyclic structure may be a substituted cyclic structure, for example, the structure may include an azepane moiety or a cycloheptane structure, or the structure may include a cycloalkone moiety, that is, an oxygen atom that is double bonded to a member of the cyclic ring.

An "amino acid" is given its ordinary meaning as used in the field of biochemistry. An amino acid typically has a structure:

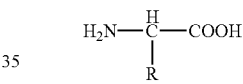

In this structure, R may be any suitable moiety. For example, R may be a hydrogen atom, a methyl group, or an isopropyl group. As used herein, the "natural amino acids" are the 20 amino acids commonly found in nature, i.e., alanine, arginine, asparagine, aspartic acid, cysteine, glutamine, glutamic acid, glycine, histidine, isoleucine, leucine, lysine, methionine, phenylalaine, proline, serine, threonine, tryptophan, tyrosine, and valine. Similarly, an unnatural amino acid is an amino acid, where the R group does not correspond to one of the natural amino acids.

In one embodiment, the compositions further comprise homologs, analogs, derivatives, enantiomers and functionally equivalent compositions thereof of the compositions of the invention, for example, compositions 1-51. Such homologs, analogs, derivatives, enantiomers and functionally equivalent compositions thereof of the compositions may be used in any of the assays described above that are able to detect or treat cancer, particularly MUC1-associated cancers. "Functionally equivalent" generally refers to a composition capable of treatment of patients having MUC1-associated cancer, or of patients susceptible to MUC1-associated cancers. It will be understood that the skilled artisan will be able to manipulate the conditions in a manner to prepare such homologs, analogs, derivatives, enantiomers and functionally equivalent compositions.

Homologs, analogs, derivatives, enantiomers and functionally equivalent compositions which are about as effective or more effective than the parent compound are also intended for use in the method of the invention. Such compositions may also be screened by the assays described herein for increased potency and specificity towards the cancer characterized by aberrant expression of MUC1, preferably with limited side effects. Synthesis of such compositions may be accomplished through typical chemical modification methods such as those routinely practiced in the art.

Another aspect of the present invention involves a method comprising providing any of the compositions of the present invention, and performing a combinatorial synthesis on the composition, preferably to obtain homologs, analogs, derivatives, enantiomers and functionally equivalent compositions thereof of the composition. An assay may be performed with the homolog, analog, derivative, enantiomer or functionally equivalent composition to determine its effectiveness in inhibiting cancer characterized by aberrant expression of MUC1. The combinatorial synthesis can involve subjecting a plurality of the compositions described herein to combinatorial synthesis.

Another aspect provides a method of administering any composition of the present invention to a subject. When administered, the compositions of the invention are applied in pharmaceutically acceptable amounts and as pharmaceutically acceptable compositions. Such preparations may routinely contain salts, buffering agents, preservatives, compatible carriers or other therapeutic ingredients. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers, or will be able to ascertain such, using only routine experimentation.

In some cases, the present invention includes the step of bringing a composition of the invention into association or contact with a suitable carrier, which may constitute one or more accessory ingredients. The final compositions may be prepared by any suitable technique, for example, by uniformly and intimately bringing the composition into association with a liquid carrier, a finely divided solid carrier or both, optionally with one or more formulation ingredients such as buffers, emulsifiers, diluents, excipients, drying agents, antioxidants, preservatives, binding agents, chelating agents, or stabilizers and then, if necessary, shaping the product.

In some embodiments, the compositions of the present invention may be present as a pharmaceutically acceptable salt. The term "pharmaceutically acceptable salts" includes salts of the composition, prepared, for example, with acids or bases, depending on the particular substituents found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galactunoric, salicylic, formic, naphthalene-2-sulfonic, and the like. Still other suitable acids include amino acids such as arginate, aspartate, glutamate, and the like.

In general, pharmaceutically acceptable carriers for are well-known to those of ordinary skill in the art. As used herein, a "pharmaceutically acceptable carrier" refers to a non-toxic material that does not significantly interfere with the effectiveness of the biological activity of the active ingredient or ingredients. Pharmaceutically acceptable carriers include, for example, diluents, emulsifiers, fillers, salts, buffers, excipients, drying agents, antioxidants, preservatives, binding agents, bulking agents, chelating agents, stabilizers, solubilizers, and other materials well-known in the art. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodiumalginate, polyvinylpyrrolideone; dispersing or wetting agents such as lecithin or other naturally-occurring phosphatides; or thickening agents such as cetyl alcohol or beeswax. The compositions of the invention may be formulated into preparations in solid, semi-solid, liquid or gaseous forms such as tablets, capsules, elixrs, powders, granules, ointments, solutions, depositories, inhalants or injectables. The compositions of the present invention may be delivered by any suitable delivery method, for example, oral, parenteral or surgical administration. The invention also embraces locally administering the compositions of the invention, for example, as implants Preparations include sterile aqueous or nonaqueous solutions, suspensions and emulsions. Examples of nonaqueous solvents are propylene glycol, polyethylene glycol, vegetable oil such as olive oil, an injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, (such as those based on Ringer's dextrose), and the like. Preservatives and other additives may also be present such as, for example, antimicrobials, antioxidants, chelating agents and inert gases and the like. Those of skill in the art can readily determine the various parameters for preparing these pharmaceutical compositions without resort to undue experimentation.

The compositions of the invention may be administered singly or in combination with other compositions of the invention or other compositions. For example, in one embodiment, compositions of the invention are administered in combination with agents that block cell surface receptors, such as the alpha-V-beta-3 cell surface receptor.

According to the methods of the invention, the compositions of the invention can be administered by injection by gradual infusion over time or by any other medically acceptable mode. Any medically acceptable method may be used to administer the composition to the patient. The particular mode selected will depend of course, upon factors such as the particular drug selected, the severity of the state of the subject being treated, or the dosage required for therapeutic efficacy. The methods of this invention, generally speaking, may be practiced using any mode of administration that is medically acceptable, meaning any mode that produces effective levels of the active composition without causing clinically unacceptable adverse effects.

The administration may be localized (i.e., to a particular region, physiological system, tissue, organ, or cell type) or systemic, depending on the condition to be treated. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be preferred for some treatments because of the convenience to the patient as well as the dosing schedule. Compositions suitable for oral administration may be presented as discrete units such as capsules, pills, cachettes, tables, or lozenges, each containing a predetermined amount of the active compound. Other oral compositions include suspensions in aqueous or non-aqueous liquids such as a syrup, an elixir, or an emulsion.

The compositions of the present invention may be given in dosages, generally, at the maximum amount while avoiding or minimizing any potentially detrimental side effects. The compositions can be administered in effective amounts, alone or in a cocktail with other compounds, for example, other compounds that can be used to treat cancer. An effective amount is generally an amount sufficient to inhibit MUC1-associated cancer within the subject.

One of skill in the art can determine what an effective amount of the composition is by screening the ability of the composition using any of the assays described herein. The effective amounts will depend, of course, on factors such as the severity of the condition being treated; individual patient parameters including age, physical condition, size and weight; concurrent treatments; the frequency of treatment; or the mode of administration. These factors are well known to those of ordinary skill in the art and can be addressed with no more than routine experimentation. It is generally preferred that a maximum dose be used, that is, the highest safe dose according to sound medical judgment.

Dosages may be estimated based on the results of experimental models, optionally in combination with the results of assays of the present invention. Generally, daily oral prophylactic doses of active compounds will be from about 0.01 mg/kg per day to 2000 mg/kg per day. Oral doses in the range of 10 to 500 mg/kg, in one or several administrations per day, may yield suitable results. In the event that the response of a particular subject is insufficient at such doses, even higher doses (or effective higher doses by a different, more localized delivery route) may be employed to the extent that patient tolerance permits. Multiple doses per day are also contemplated in some cases to achieve appropriate systemic levels of the composition.

In administering the compositions of the invention to subjects, dosing amounts, dosing schedules, routes of administration and the like may be selected so as to affect other known activities of these compositions. For example, amounts, dosing schedules and routes of administration may be selected as described herein, whereby therapeutically effective levels for the inhibition or treatment of MUC1-associated cancers are provided, yet therapeutically effective levels for alternative treatments are not provided.

Other delivery systems suitable for use with the present invention include time-release, delayed release, sustained release, or controlled release delivery systems. Such systems may avoid repeated administrations of the active compounds of the invention in many cases, increasing convenience to the subject and the physician. Many types of release delivery systems are available and known to those of ordinary skill in the art. They include, for example, polymer based systems such as polylactic and/or polyglycolic acid, polyanhydrides, and polycaprolactone; nonpolymer systems that are lipid-based including sterols such as cholesterol, cholesterol esters, and fatty acids or neutral fats such as mono-, di- and triglycerides; hydrogel release systems; silastic systems; peptide based systems; wax coatings; compressed tablets using conventional binders and excipients; or partially fused implants. Specific examples include, but are not limited to, erosional systems in which the composition is contained in a form within a matrix, or diffusional systems in which an active component controls the release rate. The formulation may be as, for example, microspheres, hydrogels, polymeric reservoirs, cholesterol matrices, or polymeric systems. In some embodiments, the system may allow sustained or controlled release of the active compound to occur, for example, through control of the diffusion or erosion/degradation rate of the formulation. In addition, a pump-based hardware delivery system may be used in some embodiment of the invention.

Use of a long-term release implant may be particularly suitable in some cases. "Long-term release," as used herein, means that the implant is constructed and arranged to deliver therapeutic levels of the composition for at least 30 or 45 days, and preferably at least 60 or 90 days, or even longer in some cases. Long-term release implants are well known to those of ordinary skill in the art, and include some of the release systems described above.

The present invention also provides any of the above-mentioned compositions useful for treatment of cancer characterized by aberrant expression of MUC packaged in kits, optionally including instructions for use of the composition for the treatment of cancer. That is, the kit can include a description of use of the composition for participation in any biological or chemical mechanism disclosed herein associated with cancer or tumor. The kits can further include a description of activity of cancer characterized by aberrant expression of MUC1 in treating the pathology, as opposed to the symptoms of the cancer. That is, the kit can include a description of use of the compositions as discussed herein. The kit also can include instructions for use of a combination of two or more compositions of the invention. Instructions also may be provided for administering the drug by any suitable technique, such as orally, intravenously, directly into the cerebrospinal fluid via a spinal drip, pump or implantable delivery device, or via another known route of drug delivery. The invention also involves promotion of the treatment of cancer characterized by aberrant expression of MUC1 according to any of the techniques and compositions and composition combinations described herein.

The compositions of the invention, in some embodiments, may be promoted for treatment of abnormal cell proliferation, cancers, or tumors, particularly MUC1-associated cancers or includes instructions for treatment of accompany cell proliferation, cancers, or tumors, particularly MUC1-associated cancers as mentioned above. In another aspect, the invention provides a method involving promoting the prevention or treatment of cancer via administration of any one of the compositions of the present invention, and homologs, analogs, derivatives, enantiomers and functionally equivalent compositions thereof in which the composition is able to treat MUC1-associated cancers. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cell proliferation, cancers or tumors. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, or homologs, analogs, derivatives, enantiomers and functionally equivalent compositions thereof, but can also include the composition of the invention and instructions of any form that are provided in connection with the composition in a manner such that a clinical professional will clearly recognize that the instructions are to be associated with the specific composition.

The kits described herein may also contain one or more containers, which can contain compounds such as the species, signaling entities, biomolecules and/or particles as described. The kits also may contain instructions for mixing, diluting, and/or administering the compounds. The kits also can include other containers with one or more solvents, surfactants, preservative and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kit, in one set of embodiments, may comprise a carrier means being compartmentalized to receive in close confinement one or more container means such as vials, tubes, and the like, each of the container means comprising one of the separate elements to be used in the method. For example, one of the container means may comprise a positive control in the assay. Additionally, the kit may include containers for other components, for example, buffers useful in the assay.

The function and advantage of these and other embodiments of the present invention will be more fully understood from the examples below. The following examples are intended to illustrate the benefits of the present invention, but do not exemplify the full scope of the invention.

EXAMPLE 1

This example illustrates high-throughput drug screen that identifies compounds able to inhibit interactions involving the MUC1 receptor and/or its ligands. A lysate is prepared from MUC1+ breast tumor cells. In the drug screening assay, described below, this lysate provides ligands and/or co-receptors that interact with the MGFR portion of the MUC1 receptor. FIG. 1 is an illustration of the drug screening assay.

A cell pellet from a cell culture flask approximately 75% confluent with T47D cells (ATCC #HTB-133—a MUC1+ breast tumor cell line) is prepared for each experiment. The cell pellet is optionally frozen at $-20°$ C. before use. The cells are pelleted at $4°$ C. in a centrifuge, and the supernatant is removed with disturbing the cells.

The cell pellet is then washed in phosphate-buffered saline and resuspended in additional cold saline. The number of cells is determined and the volume is adjusted such that the cell pellet contains approximately 1 million cells.

The cells are resuspended into 2 mL of saline, then sonicated for 30 second to lyse the cells. The lysate is then separated and pelleted in a centrifuge. The supernatant, containing soluble proteins of the cell lysate, is then removed and stored.

Colloids, which will present the MGFR portion of the MUC1 receptor, are prepared as follows. 6 mL of Auro dye Forte gold colloids are derivatized such that the colloids bear self-assembled monolayers (SAMs) that present approximately 3% NTA-Ni$^{2+}$, using methods described in International patent application serial number PCT/US00/01997, filed Jan. 25, 2000, by Bamdad et al., entitled "Rapid and Sensitive Detection of Aberrant Protein Aggregation in Neurodegenerative Diseases" (International patent publication WO 00/43791, published Jul. 27, 2000), and International patent application serial number PCT/US00/01504, filed Oct. 21, 2000 by Bamdad, et al., "Interaction of Colloid-Immobilized Species with Species on Non-Colloidal Structures" (International patent publication WO 00/34783, published Jul. 27, 2000).

The colloids are separated into 24 aliquots, each containing 200 microliters. To 23 of the aliquots, 20 microliters of histidine tagged primary sequence (PS)MGFR peptide (GTINVHDVETQFNQYKTEAASPYNLTISDVS-VSDVPFPFSAQSGAHHHHHH) at 100 micromolar concentration, are added, and the aliquots incubated at room temperature for about 10 min. To the remaining aliquot, 20 microliters of a negative control peptide, histidine-tagged GRGDS peptide (HHHHHHSSSSGSSSSGSSSSGGRGDS-GRGDS) solution at 100 micromolar concentration are added.

The colloids are centrifuged for approximately 15 minutes. The supernatant is then removed and the colloid pellet is resuspended in 100 microliters of phosphate buffer.

The drug screen is performed as follows. Into each sample well, 65 microliters of lysate and 5 microliters of drug are added. About 30 microliters of histidine-tagged PSMGFR-presenting colloids are then added to the well. Observations of the well are recorded using a digital camera. The plate is observed for a period of about 1 hour, and color differences are noted.

The positive controls turn purple or blue, while the negative controls remain pink. If the drug does not bind to PSMGFR or MGFR or the ligand to MGFR, the well will turn purple/blue. Conversely, if the drug inhibits the interaction between MGFR and its ligand(s), the well will remain pink. Thus, this example illustrates one way to perform a MUC1 drug screening assay.

EXAMPLE 2

In this example, cells are counted in a cell proliferation assay in an embodiment of the invention.

Cells (e.g., T47D or K293) are plated in 96 well plates in 100 μL of the appropriate media to about 25% confluency. After allowing the cells to be in culture overnight, the cells are counted (in triplicate) to determine the 0 hour cell count. For this purpose, the media is removed and the cells detached with trypsin in a defined volume.

The cells are then counted using a counting chamber (e.g., a hemocytometer). To the remaining wells, 5 microliters of the specific compounds (or a control, such as dimethyl sulfoxide) are added in triplicate. After 48 hours of culture, the media is removed, then the cells detached with trypsin and counted again using a counting chamber to obtain the 48 hour cell count.

FIG. 2 is a graph showing the inhibitory effect of certain compositions of the invention on the proliferation of MUC1+ cells. The MUC1+ cells used in this experiment were T47D cells (a breast tumor cell line) and the control cells were K293 cells from an embryonic kidney cell line.

While several embodiments of the invention have been described and illustrated herein, those of ordinary skill in the art will readily envision a variety of other means and structures for performing the functions and/or obtaining the results or advantages described herein, and each of such variations or modifications is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, if such features, systems, materials and/or methods are not mutually inconsistent, is included within the scope of the present invention.

In the claims (as well as in the specification above), all transitional phrases such as "comprising," "including," "carrying," "having," "containing," "involving," and the like are to be understood to be open-ended, i.e. to mean including but not limited to. Only the transitional phrases "consisting of" and "consisting essentially of" shall be closed or semi-closed transitional phrases, respectively, as set forth in the United States Patent Office Manual of Patent Examining Procedures, section 2111.03.

What is claimed is:

1. A method of reducing proliferation of tumor cells that express cleaved form of MUC1 in which MGFR region is accessible to ligand interaction, by contacting the cells with an effective amount of a compound, which has the structure:

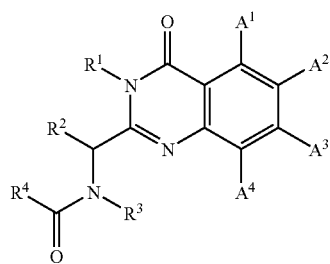

wherein $A^1$, $A^2$, $A^3$ and $A^4$ are each independently selected from the group consisting of H, lower alkyl, lower alkoxy and halogen, and $R^1$, $R^2$, $R^3$, and $R^4$ each independently comprise at least one atom.

2. The method according to claim 1, wherein $R^1$ is H or substituted or unsubstituted or branched or straight-chain alkyl.

3. The method according to 2, wherein $R^1$ is ethyl.

4. The method according to claim 1, wherein $R^1$ comprises a cyclic group, multicyclic group or a fusedcyclic group; an alkylcyclic group, an alkylmulticyclic group or an alkylfusedcyclic group; heterocyclic group, multiheterocyclic group or a fusedheterocyclic group; or a alkylheterocyclic group, a alkylheteromulticyclic group or an alkyl fusedheterocyclic group.

5. The method according to claim 4, wherein $R^1$ is substituted or unsubstituted benzyl, substituted or unsubstituted arylmethyl, or substituted or unsubstituted heteroarylmethyl.

6. The method according to claim 4, wherein $R^1$ is an alkylaryl.

7. The method according to claim 6, wherein $R^1$ is substituted or unsubstituted benzyl.

8. The method according to claim 7, wherein the substituent is independently selected from H, lower alkyl, lower alkoxy, and halogens.

9. The method according to claim 4, wherein $R^1$ is an aromatic group.

10. The method according to claim 9, wherein $R^1$ is a substituted or unsubstituted naphthyl group or substituted or unsubstituted phenyl group.

11. The method according to claim 10, wherein the substituent is independently selected from H, lower alkyl, lower alkoxy, and halogens.

12. The method according to claim 11, wherein the substituent is independently selected from H, methyl, ethyl, methoxy, ethoxy, Br, Cl, and F.

13. The method according to claim 1, wherein $R^2$ is branched or straight-chain lower alkyl.

14. The method according to claim 13, wherein $R^2$ is methyl.

15. The method according to claim 13, wherein $R^2$ is ethyl.

16. The method according to claim 13, wherein $R^2$ is iso-propyl.

17. The method according to claim 1, wherein $R^3$ is straight-chain or branched, substituted or unsubstituted alkyl, alkyl hydroxyl, alkyl amino, alkyl aryl, or alkyl heteroaryl.

18. The method according to claim 17, wherein $R^3$ is aminopropyl or dimethyl aminopropyl.

19. The method according to claim 17, wherein $R^3$ is methyl, ethyl, propyl, iso-propyl, butyl, iso-butyl, pentyl, iso-pentyl, hexyl, 2-(N,N-dimethyl amino ethyl), 2-phenylethyl, or 2-methyl furanyl.

20. The method according to claim 1, wherein $R^4$ is straight-chain or branched, substituted or unsubstituted alkyl having 1-13 carbon atoms.

21. The method according to claim 20, wherein $R^4$ is halogenated alkyl.

22. The method according to claim 21, wherein $R^4$ is dichloromethyl.

23. The method according to claim 20, wherein $R^4$ is 2,4,4-trimethylpentyl, or $C_{13}H_{27}$.

24. The method according to claim 1, wherein $R^4$ comprises a non-aromatic, bicyclic ring.

25. The method according to claim 24, wherein $R^4$ comprises adamantane.

26. The method according to claim 1, wherein $R^4$ comprises a substituted or unsubstituted aromatic, heteroaromatic, or fused heteroaromatic group.

27. The method according to claim 26, wherein $R^4$ comprises a substituted or unsubstituted phenyl, naphthyl, heteroaryl or diphenylmethyl, each of which is optionally substituted.

28. The method according to claim 27, wherein the substituent is selected from alkyl, alkoxy and halogen.

29. The method according to claim 28, wherein the substituent is selected from methyl, ethyl, methoxy, ethoxy, Br, Cl and F.

30. The method according to claim 27, wherein $R^4$ is benzodioxolane.

31. The method according to claim 26, wherein $R^4$ is a substituted or unsubstituted heteroarylmethyl, bicyclic heteroaryl, -alkylaryl, -alkylheteroaryl, or branched-alkylaryl, or branched alkylheteroaryl.

32. The method according to claim 31, wherein $R^4$ is a substituted or unsubstituted 1-phenyl-1-alkyl, or 1-phenyl-1-branched alkyl.

33. The method according to claim 31, wherein $R^4$ is 1-phenyl-1-propyl.

34. The method according to claim 1, wherein $R^4$ comprises substituted or unsubstituted nitrogen atom.

35. The method according to claim 34, wherein $R^4$ is —NH-alkyl, —NH-benzyl, —NH-aryl, —NH-alkylaryl, —NH-non-aromatic cyclic group, or —NH-fusedaryl.

36. The method according to claim 35, wherein $R^4$ is —NH-phenyl, —NH-phenyl substituted with lower alkyls and/or halogens, or —NH-naphthyl.

37. The method according to claim 34, wherein $R^4$ is substituted or unsubstituted NH-benzyl.

38. The method according to claim 1, wherein $A^1$, $A^2$, and $A^4$ are H and $A^3$ is Cl, and $R^1$ is benzyl, $R^2$ is isopropyl, $R^3$ is aminopropyl and $R^4$ is 4-methylphenyl.

39. The method according to claim 1, wherein $A^1$, $A^2$, and $A^4$ are H and $A^3$ is Cl, and $R^1$ is benzyl, $R^2$ is ethyl, $R^3$ is dimethyl aminopropyl and $R^4$ is 4-bromophenyl.

40. The method according to claim 1, wherein the tumor cells are colon cancer cells.

41. A method of reducing proliferation of tumor cells that express cleaved form of MUC1 in which MGFR region is accessible to ligand interaction comprising:
(i) assaying tumor cells for the presence of the cleaved form of MUC1 in which MGFR region is accessible to ligand interaction; and
(ii) if the tumor cells are positive for the presence of the cleaved form of MUC1 in which MGFR region is accessible to ligand interaction, contacting the cells with an effective amount of a compound, which has the structure:

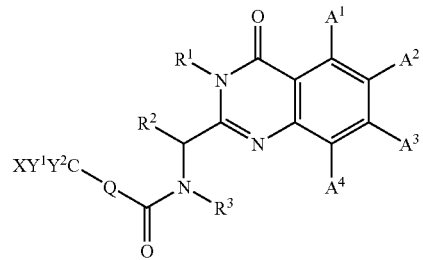

wherein $A^1$, $A^2$, $A^3$ and $A^4$ are each independently selected from the group consisting of H, lower alkyl, lower alkoxy and halogen, and
$R^1$, $R^2$, $R^3$, and $R^4$ each independently comprise at least one atom.

* * * * *